(12) United States Patent
Hakonarson

(10) Patent No.: US 7,148,008 B2
(45) Date of Patent: Dec. 12, 2006

(54) METHODS FOR PREDICTING DRUG SENSITIVITY IN PATIENTS AFFLICTED WITH AN INFLAMMATORY DISEASE

(75) Inventor: Hakon Hakonarson, Reykjavik (IS)

(73) Assignee: deCode genetics ehf., Reykjavik (IS)

( * ) Notice: Subject to any disclaimer, the term of this patent is extended or adjusted under 35 U.S.C. 154(b) by 431 days.

(21) Appl. No.: 10/234,652

(22) Filed: Sep. 3, 2002

(65) Prior Publication Data

US 2003/0134776 A1 Jul. 17, 2003

Related U.S. Application Data

(63) Continuation-in-part of application No. 09/947,991, filed on Sep. 6, 2001.

(51) Int. Cl.
*C12Q 1/68* (2006.01)
(52) U.S. Cl. ........................................................ 435/6
(58) Field of Classification Search .................... 435/6; 536/23.1, 24.3, 24.31
See application file for complete search history.

(56) References Cited

U.S. PATENT DOCUMENTS

| | | | |
|---|---|---|---|
| 6,801,859 B1 | 10/2004 | Friend et al. | |
| 2002/0151588 A1 | 10/2002 | Thomson et al. | |
| 2003/0054362 A1 | 3/2003 | Mohanlal | |
| 2003/0113831 A1 | 6/2003 | Hakonarson | |
| 2003/0154032 A1 | 8/2003 | Pittman et al. | |
| 2003/0204090 A1* | 10/2003 | Ono et al. | 546/138 |

FOREIGN PATENT DOCUMENTS

| | | |
|---|---|---|
| WO | WO 00/39336 | 7/2000 |
| WO | WO 02/059367 A2 | 1/2002 |
| WO | WO 03/021261 A3 | 3/2003 |

OTHER PUBLICATIONS

Villeneuve et al. Current Topics in Medicinal Chemistry, vol. 4, No. 13, pp. 1453-1458, 2004 (Abstract only).*
Arend, W., "Physiology of Cytokine Pathways in Rheumatoid Arthritis," *Arthritis Care and Research* 45:101-106 (2001).
Barnes, P. et al., "Efficacy and Safety of Inhaled Corticosteroids," *Am. J. Respir. Crit. Care. Med.* 157:S1-S53 (1998).
Broide, D. et al., "Cytokines in Symptomatic Asthma Airways," *J. Allergy Clin. Immunol.* 89:958-967 (1992).
Eggleston, P. and Bush, R., "Environmental allergen avoidance: An Overview," *J. Allergy Clin. Immunol.* 107:S403-5 (2001).
"Genes for Asthma? An Analysis of The European Community Respiratory Health Survey," *Am. J. Respir. Crit. Care Med.* 156:1773-1780 (1997).
Golub, T., et al., "Molecular Classification of Cancer: Class Discovery and Class Prediction by Gene Expression Monitoring," *Science* 286: 531-537 (1999).
Gulcher, J. and Stefansson, K., "Population Genomics: Laying the Groundwork for Genetic Disease Modeling and Targeting," *Clin. Chem. Lab. Med.* 36: 523-527 (1998).

Grunstein M. et al. "Autocrine signaling by IL-10 mediates altered resonsiveness of atopic sensitized airway smooth muscle," *Am. J. Physiol. Lung Cell. Mol. Physiol.* 281: L1130-7 (2001).
Hakonarson, H. et al. "Autocrine Role of Interleukin 1β in Altered Responsiveness of Atopic Asthmatic Sensitized Airway Smooth Muscle," *J. Clin. Invest.* 99: 117-124 (1997).
Hakonarson, H. et al. "Mechanism of Rhinovirus-induced Changes in Airway Smooth Muscle Responsiveness," *J. Clin. Invest.* 102: 1732-1741 (1998).
Hakonarson, H. et al. "Autocrine interation between Il-5 and IL-1β mediates altered responsiveness of atopic asthmatic sensitized airway smooth muscle," *J. Clin. Invest.* 104: 657-667 (1999).
Hakonarson, H. et al. "Association between Il-1beta/TNF-alpha Induced Glucocorticoid-Sensitive Changes in Multiple Gene Expression and Altered Responsiveness in Airway Smooth Muscle," *Am. J. Respir. Cell Mol. Biol.* 25: 761-71 (2001).
Leung, D. and Chrousos, G., "Is There a Role for Glucocorticoid Receptor Beta in Glucocorticoid-dependent Asthmatics," *Am. J. Respir. Crit. Care Med.* 162: 1-3 (2000).
Keller, A., et al., "Bayesian classification of DNA array expression data," Technical report, Department of Computer Science and Engineering, University of Washington (Aug. 2000).
Heller, Renu A. et al., "Discovery and Analysis of Inflammatory Disease-Related Genes Using cDNA Microarrays," *Proc. Natl. Acad. Sci. USA*, 94:2150-2155 (1997).
Clarke, P., et al., "Gene Expression Profiling of Human Colon Cancer Cells Following Inhibition of Signal Transduction by 17-Allylamino-17-Demethoxygeldanamycin, an Inhibitor of the hsp90 Molecular Chaperone," *Oncogene*, 19:4125-4133 (2000).
Galon, J., et al., "Gene Profiling Reveals Unknown Enhancing and Suppressive Actions of Glucocorticoids on Immune Cells," *FASEB Journal*, 16:61-71 (2002).
Heyninck, K., et al., "The Cytokine-Inducible Zinc Finger Protein A20 Inhibits IL-1 Induced NF-κB Activation at the Level of TRAF6," *FEBS*, 442:147-150 (1999).
Khoo, C., et al., "Differential Expression of Cysteine-rich Intestinal Protein in Liver and Intestine in $CCl_4$-Induced Inflammation," *American Physiological Society*, 270:G613-G618 (1996).

(Continued)

*Primary Examiner*—Kenneth R. Horlick
(74) *Attorney, Agent, or Firm*—Hamilton, Brook, Smith & Reynolds, P.C.

(57) ABSTRACT

Methods are disclosed for predicting the efficacy of a drug for treating an inflammatory disease in a human patient, including: obtaining a sample of cells from the patient; obtaining a gene expression profile of the sample in the absence and presence of in vitro modulation of the cells with specific cytokines and/or mediators; and comparing the gene expression profile of the sample with a reference gene expression profile, wherein similarities between the sample expression profile and the reference expression profile predicts the efficacy of the drug for treating the inflammatory disease in the patient.

10 Claims, 5 Drawing Sheets

OTHER PUBLICATIONS

Saban, M., et al., "Time Course of LPS-Induced Gene Expression in a Mouse Model of Genitourinary Inflammation," *Physiol. Genomics*, 5:147-160 (2001).

Sutherland, A., "Gene Expression Analysis in Immunmodulatory and Inflammatory Model Systems Using Affymetrix Genechip Expression Arrays," *Cell Biology International*, 24:975 (2000), abstract.

Ahmed, S., et al., "Novel Polymorphism in the Coding Region of the IL-13 Receptor Alpha' Gene: Association Study with Atopic Asthma in the Japanese Population," *Exp. Clin. Immunogenet.* 17:18-22 (2000).

Asher, B., *J. Mol. Graph Model.*, 18:79-82 (2000).

Gagliardo, R. et al., "Glucocorticoid Receptor $\alpha$ and $\beta$ in Glucocorticoid Dependent Asthma," *Am. J. Respir. Crit. Care Med.*, 162:7-13 (2000).

"Guidelines for the Diagnosis and Management of Asthma": Expert Panel Report 2, Jul. 1997, National Institutes of Health, NIH Publication No. 97-4051 (1997). U.S. Government Printing Office, Washington, D.C.

Heinzmann, A. et al., "Genetic variants of IL-13 signalling and human asthma and atopy," *Hum. Mol. Genet.*, 9:549-59 (2000).

Kauppi, P. et al., "The IL9R region contribution in asthma is supported by genetic association in an isolated population," *Eur. J. Hum. Genet.*, 8:788-92 (2000).

"Standardization of Spirometry", American Thoracic Society, (1994 update), *Am. J. Respir. Crit. Care. Med.*, 152:1107-1136 (1995).

Malnistrom, et al., "Oral Montelukast, Inhaled Beclomethasone, and Placebo for Chronic Asthma," *Annals Internal Medicine*, vol. 130, pp. 487-495 (1999).

\* cited by examiner

METHODS FOR PREDICTING DRUG SENSITIVITY IN PATIENTS AFFLICTED WITH AN INFLAMMATORY DISEASE

RELATED APPLICATION

This application is a continuation-in-part of U.S. application Ser. No. 09/947,991, filed Sep. 6, 2001. The entire teachings of the above application are incorporated herein by reference.

BACKGROUND OF THE INVENTION

The field of pharmacogenomics measures differences in the effect of medications that are caused by genetic variations. Such differences are manifested by differences in the therapeutic effects or adverse events of drugs. For most drugs, the genetic variations that potentially characterize drug-responsive patients from non-responders remain unknown.

SUMMARY OF THE INVENTION

The present invention relates to methods for determining a patient's responsiveness to treatment for asthma and related inflammatory conditions.

In one embodiment, the invention is directed to a method for predicting the efficacy of a drug for treating an inflammatory disease in a human patient, comprising: obtaining a sample of cells from the patient; obtaining a gene expression profile of the sample in the absence and presence of in vitro modulation of the cells with specific mediators; and comparing the gene expression profile of the sample with a reference gene expression profile, such that similarities between the sample expression profile and the reference expression profile predicts the efficacy of the drug for treating the inflammatory disease in the patient. The reference gene expression profile can comprise expression levels of one or more informative genes listed in Tables 1, 2A, 2B, 4A, 4B and 5A–5E. The similarity between the sample expression profile and the reference expression profile predicts the efficacy of the drug for treating the inflammatory disease in the patient. In a particular embodiment, the sample is exposed to the drug for treating the inflammatory disease prior to obtaining the gene expression profile of the sample. In a particular embodiment, the sample is exposed to the drug for treating the inflammatory disease prior to obtaining the gene expression profile of the sample. The inflammatory disease can be asthma, atopy, rheumatoid arthritis, juvenile chronic arthritis, psoriasis, inflammatory bowel disease (IBD) and sepsis. The atopic inflammatory disease can be rhinitis, conjunctivitis, dermatitis and eczema. Drugs can be corticosteroids, β2-agonists and leukotriene antagonists for asthma. In addition, for inflammatory diseases, the drug can be a symptom reliever or anti-inflammatory drug for an inflammatory disease condition. In one embodiment, the sample of cells can be derived from peripheral blood mononuclear cells or neutrophils. In a particular embodiment, the gene expression profile of the sample can be obtained using a hybridization assay to oligonucleotides contained in, for example, a microarray. In another embodiment, the expression profile of the sample can be obtained by detecting the protein product of informative genes. The detection of protein products can include the use of, for example, antibodies capable of specifically binding protein products of the informative genes. The reference expression profile can be, for example, that of cells derived from healthy, non-atopic, non-asthmatic individuals. In another embodiment, the reference expression profile can be that of cells derived from patients that do not have an inflammatory disease. In one embodiment, the cells are treated with the drug candidate before the expression profile is obtained.

In yet another embodiment, the invention is directed to a method of screening for glucocorticoid sensitivity in an asthmatic patient including: obtaining a sample of cells from the patient; obtaining a gene expression profile from the sample in the absence and presence of in vitro activation of the cells with specific cytokines (mediators); and comparing the gene expression profile of the sample with a reference gene expression profile, wherein similarity in expression profiles between the sample and reference profiles indicates glucocorticoid sensitivity in the patient from whom the sample was obtained.

In yet another embodiment, the invention is directed to a method for predicting efficacy in a human asthmatic patient of leukotriene antagonists, including: obtaining a sample of cells from the patient; obtaining a gene expression profile from the sample in the absence and presence of in vitro modulation of the cells with specific mediators; and comparing the gene expression profile of the sample with a reference gene expression profile, wherein similarity in expression profiles between the sample and reference profiles predicts the efficacy in the human asthmatic patient of leukotriene antagonists.

In another embodiment, the invention is directed to an expression profile comprising expression levels of gene products from one or more genes described in Tables 1, 2A, 2B, 4A, 4B and 5A–5E.

In another embodiment, the invention is directed to a method for predicting the efficacy in a human asthma patient of leukotriene antagonists including, but not limited to, montelukast (a.k.a., SINGULAIR™; Merck, Whitehouse Station, N.J.), zafirlukast (a.k.a., ACCOLATE™, AstraZeneca, Wilmington, Del.), and zileuton (a.k.a., ZYFLO™; Abbott Laboratories, Chicago, Ill.), comprising: obtaining a sample of cells from the patient; obtaining a gene expression profile from the sample in the absence and presence of in vitro modulation of the cells with specific mediators; and comparing the gene expression profile of the sample with a reference gene expression profile, wherein similarity in expression profiles between the sample and reference profiles predicts the efficacy in the human asthmatic patient of leukotriene antagonists.

In another embodiment, the invention is directed to a kit for predicting the efficacy of a drug for treating an inflammatory disease in a human patient according to the methods described herein comprising hybridization probes capable of hybridizing to polynucleotides corresponding to pre-determined informative genes and reagents for detecting hybridization. In a different embodiment, the invention is directed to a kit for predicting the efficacy of a drug for treating an inflammatory disease in a human patient according to the methods described herein comprising antibodies capable of specifically binding protein products of pre-selected informative genes and reagents for detecting antibody binding.

BRIEF DESCRIPTION OF THE DRAWINGS

The patent or application file contains at least one drawing executed in color. Copies of this patent or patent application publication with color drawings will be provided by the Office upon request and payment of the necessary fee.

The foregoing and other objects, features and advantages of the invention will be apparent from the following more particular description of preferred embodiments of the invention, as illustrated in the accompanying drawings.

DETAILED DESCRIPTION OF THE INVENTION

Figure 1:
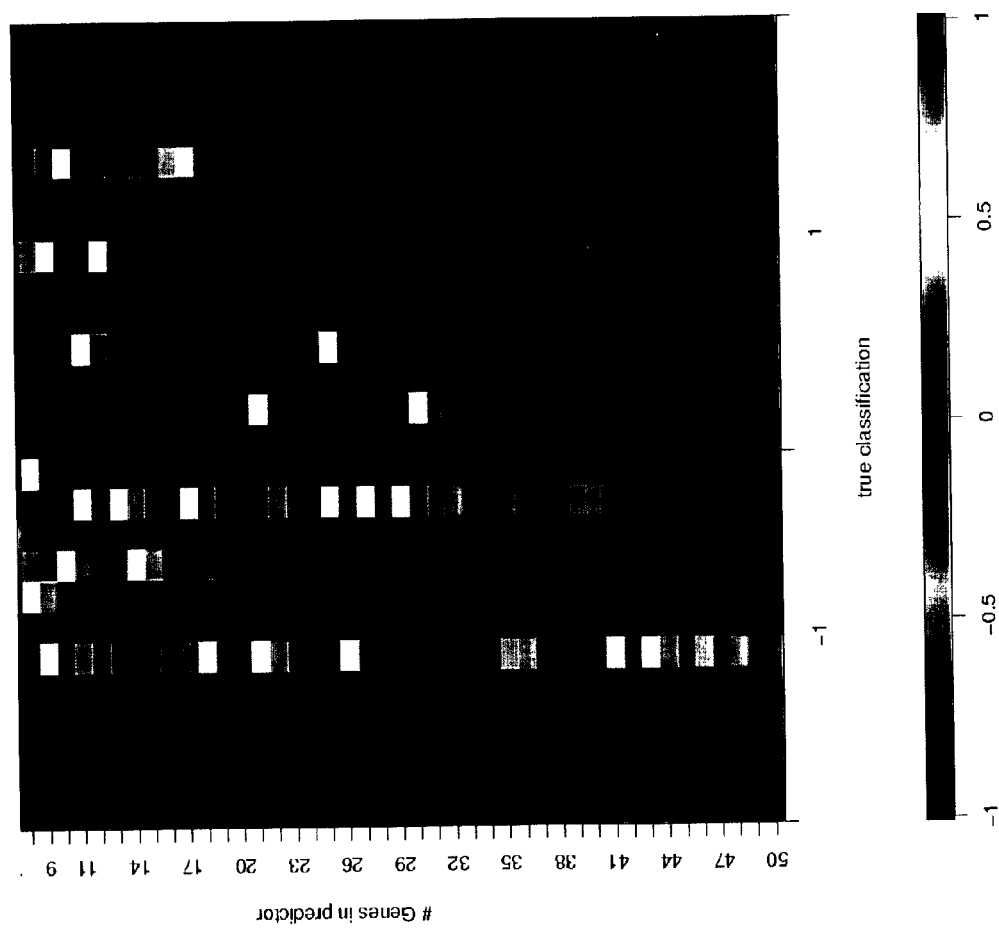
FIG. 1 is a representative Bayesian matrix plot demonstrating the predictive accuracy of a naïve Bayesian classifier in predicting drug response phenotypes of 14 glucocorticoid resistant (GC-R) and 14 glucocorticoid sensitive (GC-S) patients. The 50 genes predicted the correct drug response phenotype with 82% accuracy.

A description of preferred embodiments of the invention follows.

The present invention is directed to methods for predicting efficacy of drug treatment in asthma patients and to methods for screening drug candidates useful in treating inflammatory diseases. Current methods of treating asthma involve the use of corticosteroids, β2-agonists or leukotriene antagonists. Although asthma has been treated by these methods for several years, a significant fraction of asthma patients are resistant to treatment. As there are risks associated with methods for treating asthma, identification of patients that will be responsive to treatment is important. Methods described herein are used to identify genes that are differentially expressed in responsive patients when compared to non-responsive patients, thereby allowing for a convenient determination of patients that are responsive to treatment. Described herein are methods for activating in cultured cells obtained from patient samples and methods for utilizing said cultured cells for drug screening and obtaining expression profiles.

Asthma, or Reversible Obstructive Airway Disease (ROAD), is a condition in which the airways of the lungs become either narrowed or completely blocked, impeding normal breathing and leading to potentially more severe health problems. Although normal airways have the potential for constricting in response to allergens or irritants, the asthmatic's airways are oversensitive or hyper-reactive. In response to stimuli, the airways may become obstructed by one of the following: constriction of the muscles surrounding the airway; inflammation and swelling of the airway; or increased mucus production that clogs the airway. Once the airways have become obstructed, it takes more effort to force air through them, so that breathing becomes labored. Because exhaling through the obstructed airways is difficult, too much stale air remains in the lungs after each breath. This accumulation of stale air decreases the amount of fresh air that can be taken in with each new breath, so not only is there less oxygen available for the whole body, the high concentration of carbon dioxide in the lungs causes the blood supply to become acidic as well. This acidity in the blood may rise to toxic levels if the asthma remains untreated.

Although asthma creates difficulties in breathing and can lead to more serious problems, the lung obstruction associated with asthma is reversible, either spontaneously or with medication. Asthmatics can take anti-inflammatory agents such as corticosteroids, bronchodilators and leukotriene antagonists to reduce inflammation and asthma symptoms.

Corticosteroids are sometimes also referred to as "steroids." This type of medication is not related to the anabolic steroids that are misused by some athletes to increase performance. Rather, corticosteroids have been used as a treatment for asthma and allergies since 1948. They decrease airway inflammation and swelling in the bronchial tubes; reduce mucus production by the cells lining the bronchial tubes; decrease the chain of overreaction (hyper-reactivity) in the airways; and help the airway smooth muscle respond to other medications. Corticosteroids can be administered in a variety of ways, such as through the use of an inhaler, topically, orally, or through injection. Topical preparations (on specific surface areas such as skin or the lining of the bronchial tubes) may be applied as creams or sprays (inhalers). Corticosteroid inhalers are recommended for patients with daily, moderate or severe asthma symptoms. Oral corticosteroids and injected corticosteroids are generally only prescribed for those with severe asthma symptoms.

Although the use of corticosteroids has been commonplace for several years, they are not always effective and significant side effects do occur. Some people experience minor side effects of hoarseness and thrush (a fungal infection of the mouth and throat) from using corticosteroid inhalers. Also, long-term use of inhaled corticosteroids has been implicated in reduced growth velocity in children. Oral corticosteroids can have more side effects than inhaled corticosteroids. Oral corticosteroids are prescribed for long durations only when other treatments have failed to restore normal lung function and the risks of uncontrolled asthma are greater than the side effects of the steroids. For example, prednisone, one of the most commonly prescribed corticosteroids, can lead to possible side effects of weight gain, increased appetite, menstrual irregularities and cramps, heartburn, and indigestion. Some patients experience side effects such as loss of energy, poor appetite, and severe muscle aches or joint pains when their dosage of cortisone tablets is decreased. Long-term oral corticosteroid use may cause side effects such as ulcers, weight gain, cataracts, weakened bones and skin, high blood pressure, elevated blood sugar, easy bruising and decreased growth in children. Such side effects indicate a need to accurately assess the efficacy of corticosteroid treatment in asthmatic patients.

Bronchodilators, also called "β2-agonists", are non-steroidal anti-inflammatory medications often used as short-term "rescue" medications to immediately relieve asthma symptoms. Bronchodilators include albuterol, bitolterol, pirbuterol and terbutaline. Additionally, salmeterol is a long-acting β2-agonist that is intended to be used on a long-term basis, along with an anti-inflammatory medication, for controlling asthma. Those using salmeterol should take the medication on a daily basis, even if they are feeling fine, as it prevents symptoms. Although sporadically effective, bronchodilators are not typically useful in cases of severe asthma.

Many of the cells involved in causing airway inflammation are known to produce signaling molecules within the body called "leukotrienes." Leukotrienes are responsible for causing the contraction of the airway smooth muscle, increasing leakage of fluid from blood vessels in the lung, and further promoting inflammation by attracting other inflammatory cells into the airways. Oral anti-leukotriene medications have been introduced to fight the inflammatory response typical of allergic disease. These drugs are used in the treatment of chronic asthma. Recent data demonstrates that prescribed anti-leukotriene medications can be beneficial for many patients with asthma, however, a significant number of patients do not respond to anti-leukotriene drugs.

The present invention relates to methods for determining the treatment outcome of drugs used to treat inflammatory conditions such as asthma. The methods rely on the identification of genes that are differentially expressed in samples obtained from patients and are associated with clinical responsiveness to the drug under study. The particular genes, herein referred to as "informative genes," are identified in cells that have been induced to mimic the disease condition (e.g., asthma), or in tissue samples from patients diagnosed with asthma or other inflammatory diseases. Informative genes can be identified, for example, by determining the ratio of gene expression in induced versus uninduced cells and comparing the results between patients with variable drug sensitivity. Alternatively, informative genes can be identified based on the ratio of gene expression in disease versus normal tissue samples, or, in the case of informative genes used to identify drug responsiveness, informative genes can be identified by the ratio of gene expression in cells exposed to the drug versus cells not exposed to the drug, in subjects who qualify as responders versus non-responders to the drug. A ratio of 1.0 would indicate the gene is expressed at the same level in both samples. Ratios greater than one indicate increased expression over normal or uninduced cells, whereas ratios less than one indicate reduced expression relative to normal or uninduced cells.

A subset or all informative genes can be assayed for gene expression in order to generate an "expression profile" for responsive versus non-responsive patients. As used herein, an "expression profile" refers to the level or amount of gene expression of one or more informative genes in a given sample of cells at one or more time points. A "reference" expression profile is a profile of a particular set of informative genes under particular conditions such that the expression profile is characteristic of a particular condition. For example, a reference expression profile that quantitatively describes the expression of the informative genes listed in Tables 1, 2A, 2B, 4A, 4B and 5A–5E can be used as a reference expression profile for drug treatment responsiveness. In one embodiment, expression profiles are comprised of the fifty informative genes that exhibit differential expression, and provide sufficient power to predict the responsiveness to the drug with high accuracy. Other embodiments can include, for example, expression profiles containing about 5 informative genes, about 25 informative genes, about 100 informative genes, or any number of genes in the range of about 5 to about 400 informative genes. The informative genes that are used in expression profiles can be genes that exhibit increased expression over normal cells or decreased expression versus normal cells. The particular set of informative genes used to create an expression profile can be, for example, the genes that exhibit the greatest degree of differential expression, or they can be any set of genes that exhibit some degree of differential expression and provide sufficient power to accurately predict the responsiveness to the drug. The genes selected are those that have been determined to be differentially expressed in either a disease, drug-responsiveness, or drug-sensitive cell relative to a normal cell and confer power to predict the response to the drug. By comparing tissue samples from patients with these reference expression profiles, the patient's susceptibility to a particular disease, drug-responsiveness, or drug-resistance can be determined.

The generation of an expression profile requires both a method for quantitating the expression from informative genes and a determination of the informative genes to be screened. The present invention describes screening specific changes in individuals that affect the expression levels of gene products in cells. As used herein, "gene products" are transcription or translation products that are derived from a specific gene locus. The "gene locus" includes coding sequences as well as regulatory, flanking and intron sequences. Expression profiles are descriptive of the level of gene products that result from informative genes present in cells. Methods are currently available to one of skill in the art to quickly determine the expression level of several gene products from a sample of cells. For example, short oligonucleotides complementary to mRNA products of several thousand genes can be chemically attached to a solid support, e.g., a "gene chip," to create a "microarray." Specific examples of gene chips include Hu95GeneFL (Affymetrix, Santa Clara, Calif.) and the 6800 human DNA gene chip (Affymetrix, Santa Clara, Calif.). Such microarrays can be used to determine the relative amount of mRNA molecules that can hybridize to the microarrays (Affymetrix, Santa Clara, Calif.). This hybridization assay allows for a rapid determination of gene expression in a cell sample. Alternatively, methods are known to one of skill in the art for a variety of immunoassays to detect protein gene expression products. Such methods can rely, for example, on conjugated antibodies specific for gene products of particular informative genes.

Informative genes can be identified, for example, in samples obtained from individuals identified through database screening to have a particular trait, e.g., glucocorticoid sensitivity (GC-S) or glucocorticoid resistance (GC-R). In addition, informative genes identified in cultured cells can be verified by obtaining expression profiles from samples of known asthma patients that are either responsive or non-responsive to a particular drug treatment. An example of a combination of obtaining samples from patients and searching particular databases for the genealogical and medical history of the individual from whom the sample was obtained is herein described for the genetically isolated population of Iceland.

The population of Iceland offers a unique opportunity to identify genetic elements associated with particular disorders. The unique opportunity is available due to at least three conditions: 1) the Icelandic population is genetically isolated; 2) detailed genealogical records are available; and 3)

detailed medical records have been kept dating back to 1915. The identification of differentially expressed genes in responsive versus non-responsive patients would occur after an examination of a patient's genealogical past as well as the medical records of close relatives in addition to data obtained from samples derived from the individual.

An examination of genealogical and medical records identifies modern day individuals with a family history of exhibiting a particular trait. For example, individuals can be found that are asthmatic and that respond to a particular asthma drug treatment, and an examination of a genealogical database might confirm that indeed the individual's close relatives exhibit the same traits, on average, more than the rest of the population. Thus, a tentative conclusion can be drawn that the individual in question likely has genetic determinants that could be used to identify responsive and non-responsive patients. Samples obtained from this individual, combined with samples obtained from other such individuals, are genotyped by any of the methods described above in order to identify informative genes that can subsequently be used to generate reference expression profiles.

Informative genes can also be identified ex vivo in cells derived from patient samples. For example, a tissue sample can be obtained from a patient and cells derived from this sample can be cultured in vitro. The cells can be cultured in the presence or absence of cytokines, e.g., tumor necrosis factor alpha (hereinafter, "TNFα") and interleukin 1-beta (hereinafter, "IL-1β"), or other mediators such as, for example, leukotriene receptor agonists, e.g., $LTD_4$. As used herein, "mediator" refers to a molecular signal for a particular event. Cytokines are an example of a class of mediators that are low molecular weight, pharmacologically active proteins that are secreted by one cell for the purpose of altering either its own functions (autocrine effect) or those of adjacent cells (paracrine effect). In some instances, cytokines enter the circulation and have one or more of their effects systemically. Expression profiles of informative genes can be obtained from sample-derived cells in the presence and/or absence of cytokines or other mediators, and these profiles can be compared to reference expression profiles to determine sensitivity or resistance to drug treatment. Additionally, cells can be cultured in the presence or absence of the drug itself prior to obtaining the expression profile.

Once informative genes have been identified, polymorphic variants of informative genes can be determined and used in methods for detecting disorders in patient samples based on which polymorphic variant is present in the sample (e.g., through hybridization assays or immune detection assays using antibodies specific for gene products of particular polymorphic variants).

Alternatively, the approach described above can be used to verify the utility of informative genes identified in cultured cells. Once identified, informative genes could be verified as to their predictive ability in more genetically diverse populations, thus ensuring the utility of the predictive power of these informative genes in populations in addition to the genetically isolated population of, e.g., Iceland.

The "genetic isolation" of the Icelandic population implies a low degree of allelic variation among individuals. This circumstance reduces the background in screening for differences in a population. In "genetically diverse" populations, many differences appear between individuals that might contribute to the same trait. For example, an examination of individuals responsive for asthma drug treatment might produce a finite yet large number of genetic differences with respect to non-responsive individuals. However, in a genetically diverse population, a great majority of these genetic differences are "artifactual" or background "noise signals" detected because of the diversity of the population. For a genetically isolated population, fewer differences would be expected to be found between the two groups, providing a higher probability that the differences that are discovered are likely to be directly related to the trait in question, in this case, responsiveness to asthma drug treatment. Once determined in a genetically isolated environment, the utility of informative genes and expression profiles based on those informative genes can be verified for more general use in a genetically diverse population.

As elevated levels of both TNFα and IL-1β are characteristic of asthma and other inflammatory diseases (including, but not limited to, atopy (e.g., rhinitis, conjunctivitis, dermatitis, eczema), rheumatoid arthritis, juvenile chronic arthritis, psoriasis, IBD and sepsis), cells exhibiting elevated cellular levels of these cytokines can be used to determine drug efficacy for related inflammatory diseases. As used herein, "efficacy" describes a range of effectiveness from non-effective (non-responsive) to completely effective, and degrees between the two extremes. The present invention is directed in part to comparing gene expression profiles of activated peripheral blood mononuclear (PBM) cells or neutrophils isolated from patients with asthma or related inflammatory conditions to gene expression profiles of activated control (non-asthmatic) PBM cells or neutrophils. As used herein, "activated" refers to treating cells with cytokines or other mediators of asthma or related inflammatory diseases. Such activation can be achieved by elevating levels of cytokines such as TNFα and IL-1β. Activated cells derived from patient samples can be used to screen for drug candidates as well as provide for sample and reference expression profiles useful in diagnosing asthma and other inflammatory diseases.

The cellular levels of TNFα and IL-1β can be increased by a variety of methods known in the art. For example, mammalian cells, such as PBM cells, neutrophils, synovial cells or airway smooth muscle (ASM) cells, grown in culture can be exposed to isolated and purified TNFα and IL-1β such that these cytokines are taken up by the cells (typically, exposure of about 4 hours of TNFα at a concentration of 5 ng/mL and IL-1β at a concentration of 1 ng/mL in culture will produce pro-asthma like symptoms in cultured cells). Other methods for expression of cytokines in cells grown in culture, e.g., by transfection of genes cloned into expression vectors, are known in the art.

TNF-related pathologies or diseases, as would be mimicked by the pro-inflammatory like conditions induced in the cells described herein, include, but are not limited to, inflammatory diseases or disorders, infections, neurodegenerative diseases, malignant pathologies, cachectic syndromes and certain forms of hepatitis.

Inflammatory diseases or disorders, include, but are not limited to, acute and chronic immune and autoimmune pathologies, such as, but not limited to, rheumatoid arthritis (RA), juvenile chronic arthritis (JCA), psoriasis, graft versus host disease (GVHD), scleroderma, diabetes mellitus, allergy; asthma, acute or chronic immune disease associated with an allogenic transplantation, such as, but not limited to, renal transplantation, cardiac transplantation, bone marrow transplantation, liver transplantation, pancreatic transplantation, small intestine transplantation, lung transplantation and skin transplantation; chronic inflammatory pathologies such as, but not limited to, sarcoidosis, chronic inflammatory bowel disease, ulcerative colitis, and Crohn's pathology or disease; vascular inflammatory pathologies, such as, but not limited to, disseminated intravascular coagulation, atherosclerosis, Kawasaki's pathology and vasculitis syndromes, such as, but not limited to, polyarteritis nodosa, Wegener's granulomatosis, Henoch-Schönlein purpura, giant cell arthritis and microscopic vasculitis of the kidneys; chronic active hepatitis; Sjögren's syndrome; psoriatic arthritis; enteropathic arthritis; reactive arthritis and arthritis associated with inflammatory bowel disease; and uveitis.

Infections include, but are not limited to, sepsis syndrome, cachexia (e.g., TNFα-mediated effects), circulatory collapse and shock resulting from acute or chronic bacterial infection, acute and chronic parasitic and/or infectious diseases, bacterial, viral or fungal, such as a human immunodeficiency virus (HIV), acquired immunodeficiency syndrome (AIDS) (including symptoms of cachexia, autoimmune disorders, AIDS dementia complex and infections).

Neurodegenerative diseases include, but are not limited to, demyelinating diseases, such as multiple sclerosis and acute transverse myelitis.

Malignant pathologies are associated with TNFα-secreting tumors or other malignancies involving TNFα, such as, for example, leukemias (acute, chronic myelocytic, chronic lymphocytic and/or myelodyspastic syndrome) and lymphomas (Hodgkin's and non-Hodgkin's lymphomas, such as malignant lymphomas (Burkitt's lymphoma or Mycosis fungoides)).

Cachectic syndromes and other pathologies and diseases involving excess TNFα, include, but not limited to, cachexia of cancer, parasitic disease and heart failure.

Elevated levels of TNFα are also associated with certain types of hepatitis, including, but not limited to, alcohol-induced hepatitis and other forms of chronic hepatitis.

One of skill in the art will recognize that reagents necessary to utilize the methods described herein can be contained in a kit. Such reagents as described are either commercially available (e.g., buffered solutions, chemical reagents) or produced by methods known in the art (e.g., oligonucleotides, antibodies, ligands for detection). Thus, one of skill in the art would recognize that a kit can be produced containing in appropriate compartments, for example, all reagents, probes, and materials necessary for to allow for the practice of the methods described herein.

The invention will be further described with reference to the following non-limiting examples. The teachings of all the patents, patent applications and all other publications and websites cited herein are incorporated by reference in their entirety.

EXEMPLIFICATION

Example 1

Predictive Value of Expression Profiles in Human Patients.

Asthma is a common complex disease with a variable phenotype. While the cellular and molecular mechanisms that underlie asthma remain largely unknown, elevated levels of the pleiotropic cytokines, IL-1β and TNFα, have been implicated in the pathophysiology of asthma as well as in various other inflammatory disorders (Broide, D. et al., 1992, *J. Allergy Clin. Immunol.* 89:958–967; Arend, W., 2001, *Arthritis Rheum.* 45:101–106).

It has been widely accepted that diseases such as asthma that are common in the general population and have been demonstrated to have a strong, but complex, genetic component together with variable responsiveness to drugs, present ideal candidate disease targets for pharmacogenetic research. The latter holds great promise in optimization of individual specific therapy as well as providing new targets for drug development. Improved, preferably prophylactic, treatment of asthma patients is desired because the drugs now used are not effective in all patients, allow recurrence of the symptoms in a high percentage of patients, and sometimes have severe adverse side effects. The ability to analyze the expression level of thousands of genes in a single assay, using DNA microarrays, allows for a powerful screen of multiple molecular gene pathways, simultaneously, that may elucidate differential expression in genes encoding enzymes, kinases, ion channels, and other signaling molecules that determine individual's variation in response to drugs.

Accordingly, using high-density DNA microarray analysis, differences in mRNA expression of PBM cells freshly isolated from GC-S and GC-R asthmatics were identified. The mRNAs were examined at baseline (T0) and to the combined effects of IL-1β and TNFα. Moreover, in an attempt to further elucidate those genes that may contribute to responsiveness of GC, we examined the effects of GC treatment on altered gene expression in cells that were activated by IL-1β and TNFα. The rationale for using this strategy was based on two well-established concepts. First, the symptoms of asthma are mechanistically channeled through the actions of IL-1β and TNFα. Second, glucocorticoids act in asthmatics by altering the expression of genes that are modulated by pro-inflammatory cytokines. The results provide new evidence demonstrating: 1) of 12,600 genes examined, 50 genes selected by algorithms based on the naïve Bayesian classifier predicted the correct GC-R phenotype of the 14 GC-R and 14 GC-S patients that it was trained on with 82% accuracy; 2) when a second cohort of 26 GC-R asthmatics was tested, the predictive accuracy of the classifier was 86%, and; 3) among the genes selected there were several cell signaling molecules, transcription factors and pro-inflammatory molecules potentially associated with regulation of GC responsiveness. This is the first demonstration using gene expression profiles in freshly isolated PBM cells that differentiate between GC-R and GC-S patients that provide sufficient power to predict response to glucocorticoids in asthmatics with high accuracy.

Methods and Materials

Patients. The patient population studied was selected from the private and outpatients clinics of practicing allergists at the Allergy/Immunology Division of the National University Hospital of Iceland. A total of 1185 patient records were screened for phenotypic information and analyzed with respect to the Icelandic Genealogy Database to determine the family connections of the patients. Patients carrying a diagnosis of asthma who were using inhaled glucocorticoid medications were evaluated further. Fifty-four patients age 18–70 years were initially randomly recruited to participate and were divided into two cohorts. The first cohort consisted of 14 GC-S and 14 GC-R patients, together with 14 control subjects who had no evidence of asthma or atopy and were not using inhaled GC or any other medications. Twenty-six additional patients were also collected and used as a second cohort for the predictive classifier. The study was subsequently expanded to include 96 patients (60 GC-S and 36 GC-R), of whom, 88 completed all 3 in vitro treatment conditions (baseline, IL-1β/TNFα in the absence and presence of GC). Each cohort was subsequently randomly split into two subcohorts of equal size. A random split was performed 10 times and the most informative genes that detected GC-R from GC-S patients in the training set were used as predictors for the independent patient set of equal size. Patients were allowed to use both short and long acting β2-adrenergic drugs as well as leukotriene antagonists. Medication doses of all drugs were kept unchanged for 2 weeks and the patients had to be off oral GC for minimum of 4 weeks prior to their donation of blood for the PBM cell expression studies. A single physician, who was blinded to the expression array studies, phenotyped all patients. Upon completion of physical examination, confirmation of drug response phenotypes and informed consent authorizing his/her participation in the study, the patients were asked to donate a blood sample for the study. No tests were performed in control subjects. Forty milliliters of EDTA blood was collected and peripheral blood mononuclear (PBM) cells were isolated from the rest of the blood for the experimental studies described below.

Study Inclusion Criteria. The criteria the patients had to fulfill to enter the study, included the following:

Asthma diagnosed by an allergist/pulmonologist. The approach used to diagnose asthma in Iceland concurs with that of the diagnostic asthma criteria outlined by the NHLB and the American Thoracic Society (National Institutes of Health. 1997. Guidelines for the Diagnosis and Management of Asthma: Expert Panel Report 2, July 1997, U.S. Government Printing Office, Washington, D.C. NIH Publication No. 97-4051; American Thoracic Society. Standardization of Spirometry, 1994 (update), *Am. J. Resp. Crit. Care. Med.* 1995, 152:1107–1136) and include any of the following measures:

Patient having recurrent symptoms of cough and wheezing for more than 2 years and demonstrating clinical response to bronchodilator therapy (as measured by>15% increase in Forced Expiratory Volume in 1 second (FEV1) following bronchodilator)

Patient having reduced FEV1 (FEV1<80) at baseline prior to bronchodilator therapy and showing >15% improvement in FEV1 following bronchodilator therapy Patient having recurrent symptoms of cough and wheezing and on methacholine challenge test, performed in accordance to ATS guidelines, there occurs >20% drop in FEV1 at methacholine concentrations<8 mg/L Methacholine challenge test were obtained in patients with FEV1>70. In addition, skin tests to the 12 most common aeroallergens in Iceland and total IgE levels were obtained and history and clinical evidence of rhinitis were recorded. All patients were re-examined by the same allergist who determined the clinical response to GC.

Response to inhaled glucocorticoids. Patients were categorized as either glucocorticoid sensitive (GC-S) or glucocorticoid-resistant (GC-R). Any two or more combinations of the following criteria defined glucocorticoid response in GC-S patients (Barnes, P. et al. *Am. J. Resp. Crit. Care. Med.,* 1998. 157:S1–S53):

Good control of asthma symptoms (cough and wheezing) when taking inhaled GC in recommended therapeutic doses (up to 1000 mg of Fluticasone; up to 800 mg of Budesonide; or up to 1000 mg of Beclomethasone, which were the 3 inhaled GC drugs used by the patients).

Improved exercise tolerance and/or fewer exacerbations following 8 or more weeks of therapeutic doses of inhaled GC.

Improved peak flows and/or spirometry values after 8 or more weeks of inhaled GC.

Improved quality of life/well being as judged by the patient response to a standard questionnaire, after 8 or more weeks of inhaled GC therapy.

GC-R patients did not experience improvement in the above measures when using inhaled GC in therapeutic doses. The GC-R patients had been tried on >2,000 mg of inhaled Fluticasone (or equivalent dose of Budesonide or Beclomethasone) per day. All GC-R patients studied had either moderate or severe resistance to GC therapy. The GC-R and GC-S patients were randomly split 10 times into two cohorts each, wherein one set was used for training and the other patient set was used to generate predictors for an independent set.

Study Exclusion Criteria. The study exclusion criteria are outlined below:

Therapies, which could interfere with evaluation of efficacy or the incidence of adverse effects, including:
Other investigational drugs
Concurrent medication (other than β2-adrenergic agonist or anti-leukotriene drugs).

Diseases or conditions that could interfere with the evaluation of efficacy or the incidence of adverse effects, including:
Pregnancy or lactation
Hypersensitivity or serious adverse experiences to asthma drugs in the past
Aspirin sensitive asthma
Occupational asthma
Sensitivity to the study drug or its components
Compliance to medication is of question Patient protection measures/Informed consent procedures. The 96 asthmatic patients enrolled were randomly selected from the list of 1185 asthmatic patients who fulfilled the study criteria. The response- and participation rate of the patients exceeded 95%. All patients signed an informed consent, donated blood samples, and completed a questionnaire and all tests necessary for proper phenotyping. The study was approved by the Icelandic Data Protection Commission and the National Bioethics Committee. The Data Protection Commission of Iceland subsequently encrypted personal information about the patients and their family members (Gulcher, J. and Stefansson, K. *Clin. Chem. Lab. Med.* 1998, 36:523–527). All blood and DNA samples were also coded for protection of patient's privacy.

Assessment of gene microarray expression. Ninety-six asthma patients were recruited in accordance with the study inclusion criteria. GC responsiveness was measured by scoring functions taking into account both clinical and laboratory parameters as described above. PBM cells (PBMCs) were isolated by the standardized Ficoll method. PBMCs were counted, and stained with FITC-conjugated anti-CD3 monoclonal antibodies (mAb), PE-conjugated anti-CD19 mAb, and FITC-conjugated anti-CD14 mAb and examined by flow cytometry to determine the relative contributions of each cell type. The cells were then divided into 3 treatment conditions (baseline, IL-1β/TNFα treatment and IL-1β/TNFα in the presence of GC treatment) with approximately 6 million cells per condition. Thereafter, multiple gene mRNA expression was examined in isolated PBMCs with gene microarray technology, using the human Hu95-A gene chip containing 12,600 DNA oligonucleotides (Affymetrix, Santa Clara, Calif.). In brief, cells were exposed for 4 hr to IL-1β (1 ng/mL) and TNFα (5 ng/mL) combined, or to media alone in the absence and presence of 1 hr pre-treatment with DEX ($10^{-6}$ M), and maintained at 37° C. in a humidified atmosphere of 5% $CO_2$/95% air in RMPI-1640 media. Following incubation of cells, total RNA used for the microarray expression analysis was extracted and purified using commercially available reagents recommended by the manufacturer. Total RNA was extracted using Trizol and purified with Qiagen RNAEASY spin columns (Qiagen $GmbH_2$, Germany). Approximately 5 μg of RNA were used for first and second strand cDNA synthesis. After precipitation, cDNAs were transcribed to cRNAs by methods known in the art. The biotinylated cRNA was subsequently hybridized to the Affymetrix gene chips overnight according to the manufacturer (Affymetrix, Santa Clara, Calif.). Non-bound probes were removed by high-stringency washing. The hybridized chips were developed using a Streptavidin-PE complex and scanned. The scanned images were then analysed with Affymetrix software and the data was examined using commercially available software programs (Asher B. *J. Mol. Graph Model.* 2000, 18:79–82). AvDiff values were defined by the Affymetrix software output. Fold change is defined as the ratio of AvDiff values of RNA derived from PBMCs treated with cytokines over that of untreated PBMCs. Kinetic PCR was used to correlate the mRNA expression values from the Affymetrix gene chips for several genes.

Normalization of the expression data set. The raw expression data for all genes were normalized to the trimmed mean (98%) expression values of the chip and the normalized expression value for all chips were set at 500 (Hu, J. et al., 2000. *Ann. N.Y. Acad. Sci.*, 919:9–15). The genes were also normalized to a set of 20 control (housekeeping) genes that were found to be stable during the various treatments of the samples. The analysis focused on all the genes that were expressed in the PBM cells, and, more specifically, on all genes that were significantly upregulated or downregulated by the in vitro cytokine stimulation and were subsequently reversed by glucocorticoid treatment. A predictive classifier was then applied to these genes. Three separate approaches were taken to search for predictive gene signals: 1) baseline expression values alone; 2) expression values in response to in vitro exposure to cytokines; and 3) expression values in response to cytokines in the presence of GC pre-treatment. To minimize the potential for selection bias, predictions were made for both an independent set and with the cross validation method (Ambroise, C. and McLachlan, G., 2002. *Proc. Natl. Acad. Sci. USA*, 99:6562–6566).

Classification of drug response phenotypes by naïve Bayesian classifier. A naïve Bayesian classifier (with non-informative prior) (Duda, R. and Hart, P., Pattern Classification and Scene Analysis. 1973, New York: John Wiley) was applied to test if the classification of drug response phenotypes can be achieved by expression values for a few informative genes. The classifier is trained by selecting those genes that are deemed relevant in distinguishing between phenotypes (Kellner, A. et al., Bayesian classification of DNA array expression data. Technical report, Department of Computer Science and Engineering, University of Washington, August, 2000). When a new case is presented to the classifier, the observed attribute value $x_g$ for gene g results in the odds that the presented case is glucocorticoid sensitive:

$$\frac{P(x_g/GCS)}{P(x_g/GCR)}$$

Combining the probabilities of all genes in the classifier (under the "naïve" assumption of independence) gives the total odds:

$$\frac{P(GCS)}{P(GCR)} = \prod_g \frac{P(x_g/GCS)}{P(x_g/GCR)}$$

The attributes, namely AvDiff values or fold changes, were divided into two categories (low, high) by choosing a threshold value that optimally separates phenotypes in the training set for each gene. The probability, P(x|C), was taken as the fraction of training cases of phenotype C with attribute value x. To avoid singularities due to probabilities of zero, a Laplace estimator was used, i.e., an additional case of each phenotype was added to each attribute category.

The genes used for phenotype prediction were selected by their power to separate between the phenotypes using the average of $$\frac{P(x_g|GCS)}{P(x_g|GCR)}$$

over training cases with phenotypes GC-S and GC-R, respectively, as gene score. The n genes with the highest total score (i.e., sum of scores for phenotype GC-S and GC-R) were used in the classifier. As attributes, the fold change value between baseline and cytokine induction was used. To avoid spurious fold change values, only genes with AvgDiff values>70 for baseline and cytokine induction for all individuals were considered.

Prediction of an independent patient set using the weighted voting method described by Golub et al. The GCS and GC-R patient cohorts were each randomly split into two cohorts. The random split procedure was performed 10 times with separate analyses each time. A predictor for the first cohort using a weighted voting algorithm similar to that described previously (Golub, T. et al., 1999., *Science*, 286: 531–537) by selecting genes that are deemed most relevant in distinguishing GC responders from non-responders. The weighted voting algorithm makes a weighted linear combination of relevant "informative" genes obtained in the training set to provide a classification scheme for new samples. A brief description of the algorithm follows. The mean (μ) and standard deviation (ε) for each of the two classes (Resistant and Sensitive) in the training set is first calculated. The Euclidean distance between the two classes is then calculated for each gene (x) such that $ED_x=\sqrt{(\mu_R-\mu_S)^2}$. The variance of each class is equal to the standard deviation within that class squared, $V_{R,S}=\epsilon^2$. Next, the metric used to choose the most informative genes and for the calculation of weight, for each gene, is calculated as follows: $Mx=(ED_x^2)/(V_S+V_R)$. To predict the class of a test sample Y, each gene X casts a vote for each class: $W_{XR}=M_{X}/(Y-\mu_R)^2$ and $W_{XS}=M_{X}/(Y-\mu_S)^2$. The final class of test Y is found by the lesser of $(\Sigma W_{XR})$ and $(\Sigma W_{XS})$. Thus, each gene has a vote based on its metric and the class to which its signal is closest. The class with the smallest vote at the end is the predicted class, e.g., the class the test sample is closest to using the Euclidean distance as the measure, is the predicted class. It was then determined whether an accurate prediction of drug response can be achieved by expression values of this limited set of genes for the independent cohort with no prior information using commercially available software as described previously (Shipp, M. et al., 2002. *Nat. Med.*, 8:68–74; Golub, T. et al., 1999., *Science*, 286:531–537).

Prediction of an independent patient set using the k-Nearest Neighbor algorithm. The k-Nearest Neighbor (k-NN) algorithm (Cover, T. et al., 1967. *IT,* 13:21–27) was also implemented to predict the class of a sample by calculating the Euclidean distance of the sample to the k "nearest neighbor" standardized samples in "expression" space in the training set. The class memberships of the neighbors are examined, and the new sample is assigned to the class showing the largest relative proportion among the neighbors after adjusting for the proportion of each class in the training set. The marker gene selection process was performed by feeding the k-NN algorithm only the features with higher correlation to the target class. To select genes for use in the predictor, all genes were examined individually and ranked on their ability to discriminate one class from the other using the information on that gene alone. For each gene and each class, all possible cutoff points on gene expression levels for that gene are considered to predict class membership either above or below that cutoff. Genes were scored on the basis of the best prediction point for that class. The score function is the negative logarithm of the p-value for a hypergeometric test (Fisher's exact test) of predicted versus actual class membership for this class versus all others.

Prediction using Leave One Out Cross Validation (LOOCV). In addition to vonfirmation in an independent set of patients, the genes that best separated GC responders from non-responders were selected and tested by cross-validation, wherein one patient was excluded from the data set and then a new predictor was generated from all the genes based on the remaining patients. The new predictor was then used to predict the excluded sample. The gene selection criteria was determined as described above and applied to expression values at baseline or in response to in vitro exposure to cytokines and GC.

Reagents. The cDNA Hu95 gene microarray chips and analysis system, including scanner and computer analysis software, were purchased from Affymetrix, Calif. The RPM-1640 medium was obtained from Gibco BRL (Gaithersburg, Md.). IL-1β and TNFα were obtained from R&D Systems (Minneapolis, Minn.). DEX was purchased from Sigma (St Louis, Mo.).

Results

Characteristics of patients. The patients enrolled were randomly selected from the available family clusters, which included 1185 patients, of whom over 500 were using inhaled glucocorticoids. Of the 96 patients recruited for the study, 60 were determined to be glucocorticoid sensitive and 36 were determined to be glucocorticoid resistant. Each group was split into two cohorts. The first cohort included 46 patients (training set), of whom 30 were GC-S and 18 were GC-R. The additional 46 patients were designated as the independent set, and also included 30 GC-S patients and 18 GC-R patients. The mean maintenance dose of inhaled glucocorticoids in the GC-R group was ~1,600 mg/day (range 1,000–2,000). In contrast, the GC-S patients required only intermittent or low-dose therapy (≦800 mg/day of Fluticasone or equivalent drug) of inhaled GC. Demographic information, lung function and methacholine challenge values together with atopy status are presented in Table 3. It should be noted that while the argument could be made that the asthma severity level was higher in the GC-R group, the lung function tests results were only slightly lower in the GC-R patients as compared to the GC-S patients. As shown in Table 3, the ratio of males/females and the atopy status were lower in the GC-R group, whereas the mean age was higher. Moreover, 54% GC-S and 31% of the GC-R patients were skin test positive to one or more aeroallergens. No differences were observed in the ratio of T cells, B cells and monocytes between the two groups.

Figure 2:
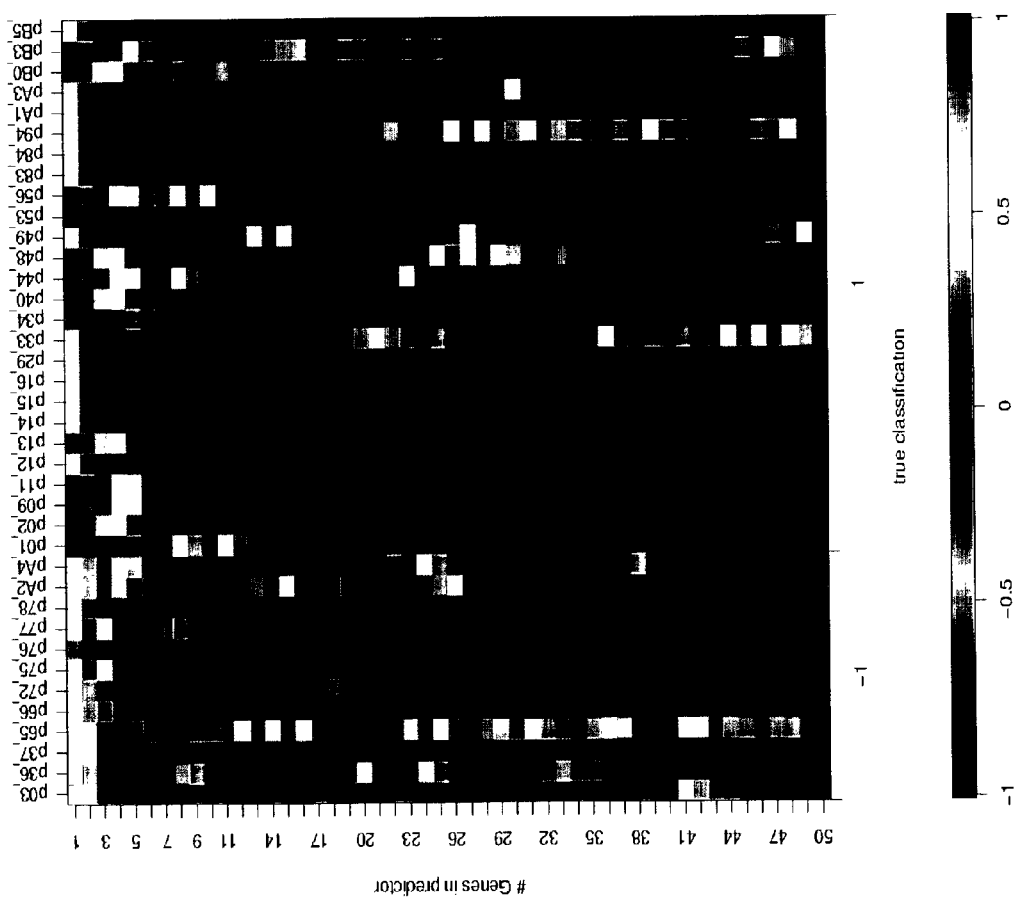
FIG. 2 is a representative Bayesian matrix plot demonstrating predictive accuracy of a naïve Bayesian classifier in predicting drug response phenotype of GC-R and GC-S patients when all 54 patients were included in training the classifier. Fifty genes were selected that predicted the correct drug response phenotype with 81% accuracy.

Performance of the Bayesian classifier with gene score selected genes. This study examined whether GC-R asthmatic patients can be identified by specific gene expression profiles in white blood cells, which are different from those obtained in patients who are GC-responders, using a naïve Bayesian classifier. The classifier was trained to select genes that best predicted between the GC-R and GC-S patient groups using all genes from the Affymetrix 12,600 Hu95 gene chip that were defined as being present and had an AvgDiff expression values>70. The latter requirement reduced the total number of genes to 5,011. Thus, the classifier was trained on 5,011 genes with the goal of identifying genes that demonstrated differences between the two groups in either their AvgDiff or fold change expression values at baseline (BL) or in response to cytokine or GC treatment. Fold change mRNA expression values in response to cytokine treatment of 50 genes distinguished a randomly selected subgroup of 14 GC-R and 14 GC-S patients with 82% accuracy. Neither baseline expression values nor fold change expression in response to GC improved the classifier's ability to discriminate between the two patient groups. The prediction of the drug response phenotype was done by the "leave-one-out cross validation" (LOOCV) method, wherein each training case is left out in turn and predicted by a classifier trained on the remaining training cases only. The percentage of the left-out training cases that were predicted correctly is then taken as an estimate of the classifier's accuracy for previously unseen cases. As shown in FIG. 1, 12 of the 14 GC-S and 11 of the 14 GC-R patients are correctly predicted. Moreover, when the classifier was trained on all of the patients, its predictive accuracy of determining the correct GC-response phenotype using the LOOCV method was essentially unchanged or 81% (FIG. 2).

Figure 3:
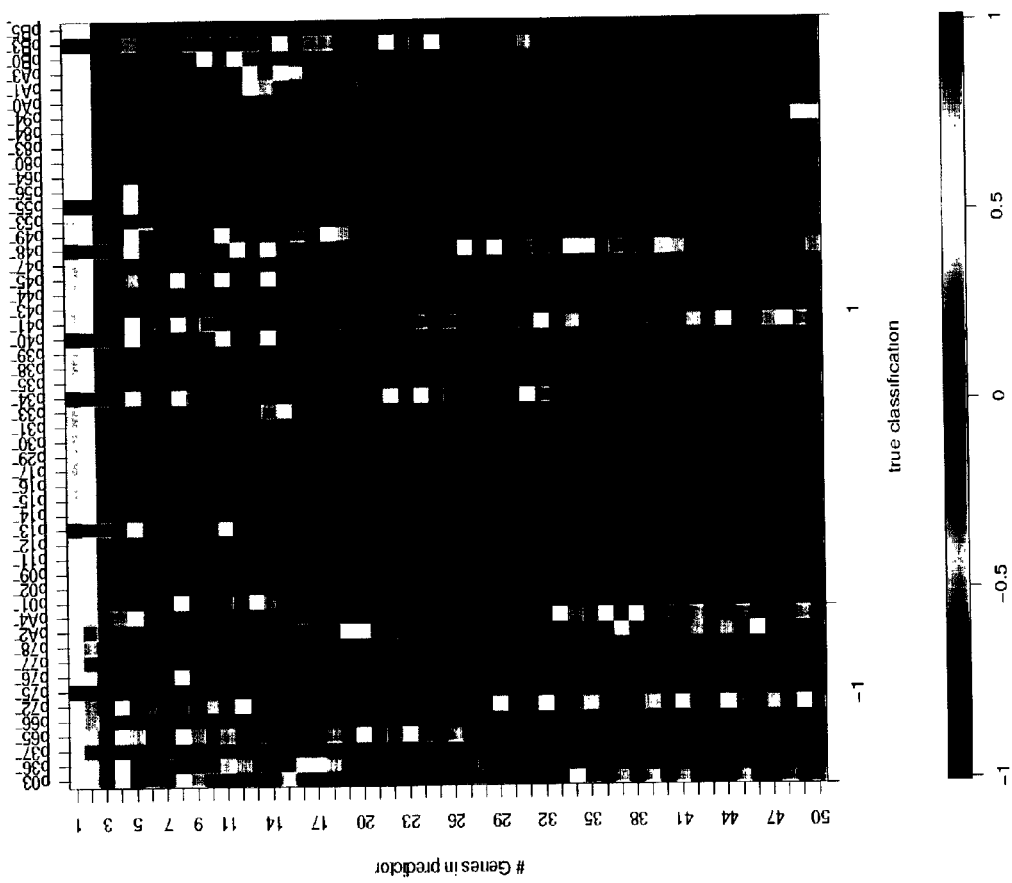
FIG. 3 is a representative Bayesian matrix plot demonstrating the predictive accuracy of a naïve Bayesian classifier in predicting a drug response phenotype of an independent cohort of 14 GC-R patients that were not used in the process of gene selection or in training of the classifier. The 50 genes selected predicted the correct drug response phenotype with 86% accuracy.
Figure 4:
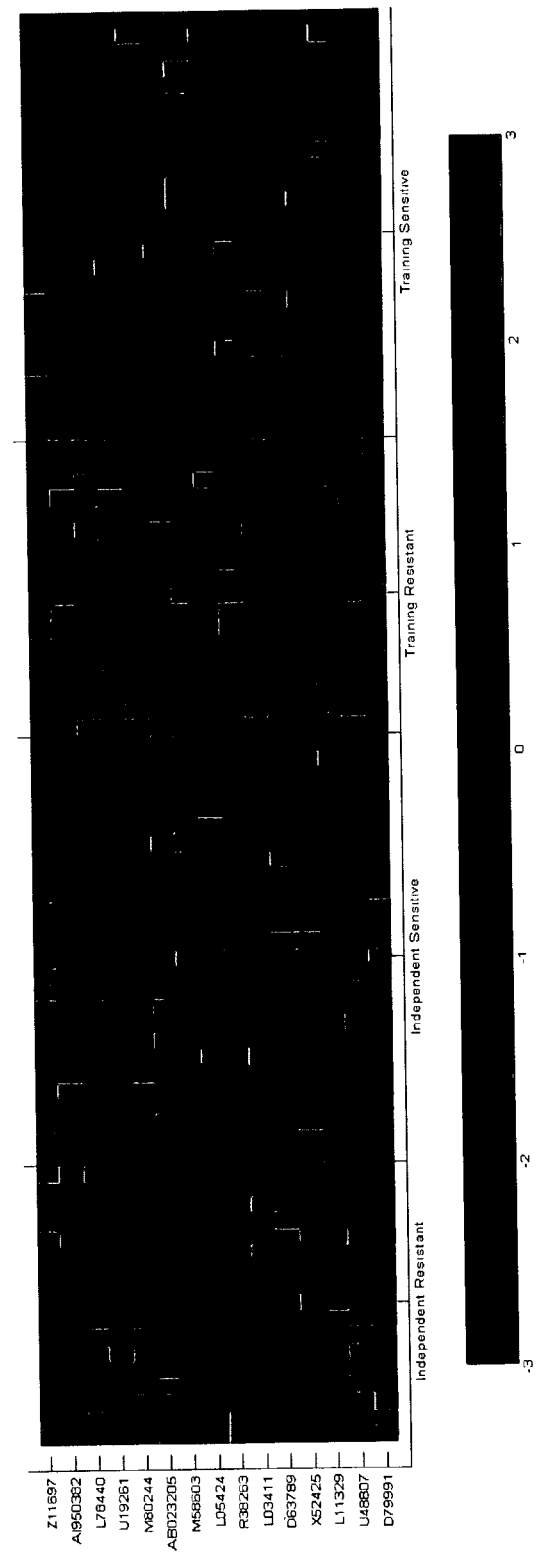
FIG. 4 is a representative matrix plot showing the differential expression of 15 genes (see Table 5) that were examined in 88 patients. In addition to the genes listed above, all of which carry a predicted weight, these 15 genes most accurately differentiated a cohort of GC responders from non-responders using the induction time point for the training set. Together, these genes predicted the correct GC response phenotype of an independent patient cohort of equal size with 86% accuracy.
Figure 5:
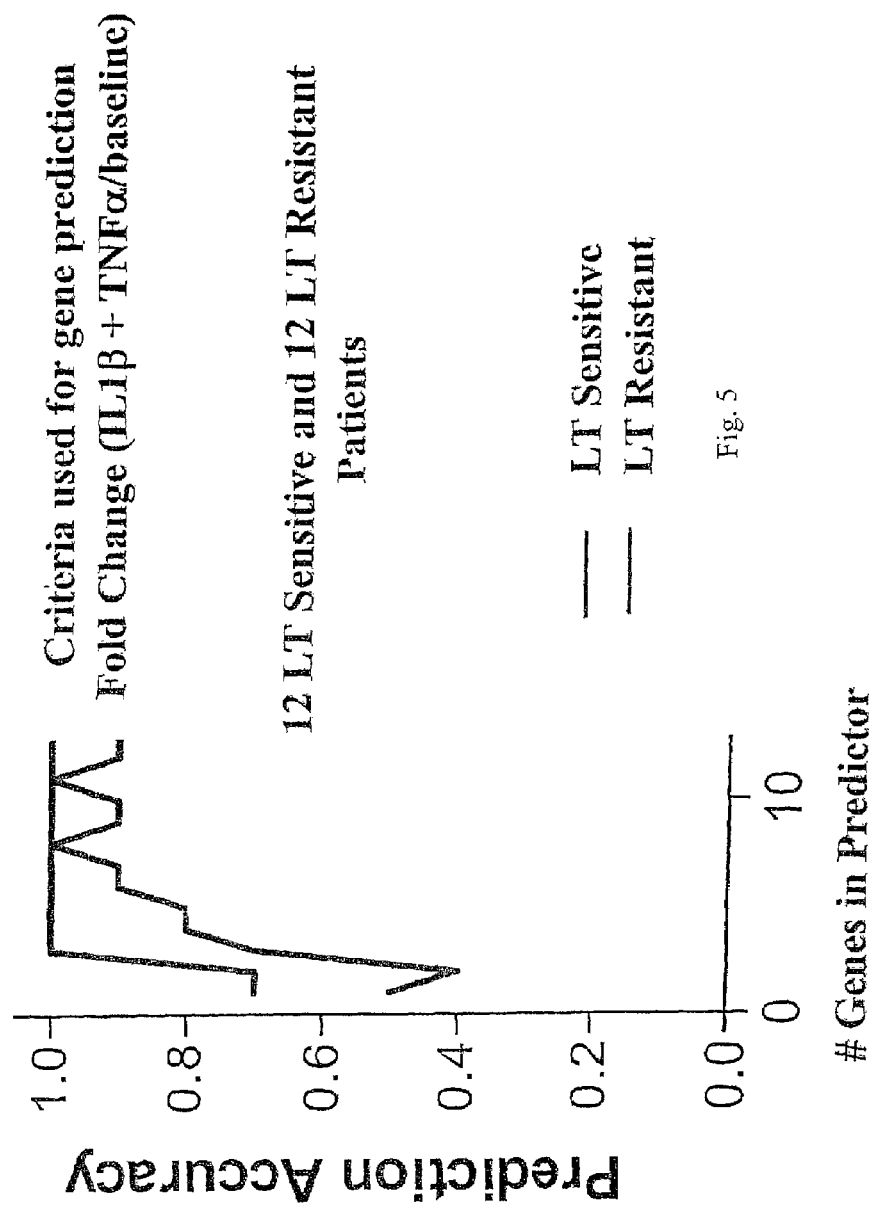
FIG. 5 is a plot demonstrating predictive accuracy of a naïve Bayesian classifier in predicting the drug response phenotype of a cohort of 12 Leukotriene Sensitive (LT-S) and 12 Leukotriene Resistant (LT-R) patients using the "leave one out cross validation" (LOOCV) method. The 12 genes selected predicted the correct drug response phenotype with over 90% accuracy.

Since these 50 genes discriminated between the drug response phenotypes with high accuracy, they may potentially have stronger power to predict the drug response phenotype for individuals within the group itself. Thus, the ability of these genes to predict the drug response phenotype of a separate cohort of patients that was not used to train the classifier was examined. As shown in FIG. 3, when the classifier was trained on the 40 GC-S versus GC-R patients, and then used to predict the an independent patient set, the predictive accuracy obtained rose to 86%.

Fifty genes contributed to the predictive power that discriminated between GC responders and non-responders. These genes are categorically displayed in Tables 1, 2A and 2B. Data on 14 control subjects with unknown GC-response profile is also included. As shown, the pattern of mRNA expression in the control group was comparable to that of the GC-S patients. This is not surprising since up to 90% of asthma patients in general are GC-responders. The genes in each category (notably CAM/ECMs, cell signaling/metabolism molecules, transcription factors and ESTs) are identified by their GenBank accession numbers, and their respective magnitudes of mean fold change of altered mRNA expression in response to cytokines.

To ensure that the gene signals that most accurately discriminate between GC responders and non-responders were captured, the groups were expanded to 96 patients (60 GC-S and 36 GC-R) and the weighted voting and k-NN algorithms were applied to both randomly split cohorts of GC-S and GC-R patients with and without cross validation.

Apart from the genes in Tables 1, 2A and 2B, 15 additional genes shown in Table 4 increased the predictive accuracy for the independent set to 86%, and the accuracy of discriminating GC responders from non-responders amounted to 89% with cross validation in all patients.

Discussion

While drug treatment remains a mainstay of medicine, in most cases a given drug has little or no effect in the majority of patients, or unforeseen serious side effects occur. For the patient this represents a dangerous and potentially life-threatening situation and, at the societal level, adverse drug reactions represent a leading cause of disease and death. Genetic variation often underlies poor response or side effects. Indeed, there already exist several examples of such correlation, including but not limited to patients variability in response to Dicumarol, Warfarin or Isoniazid due to polymorphisms in the Cyt P450 gene that confer rapid versus slow acetylating of these drugs. Given that these genetic variations may be reflected in differences in regulatory functions of these genes, variability in the mRNAs and/or protein expressions of these genes would be expected. Pharmacogenomics holds the promise that one may soon be able to profile variations between individuals' genetic makeup that accurately predict responses to drugs, addressing both efficacy and safety issues. In this connection, the ability to analyze the expression levels of thousands of genes in a single assay by DNA microarray technology provides a powerful screen of multiple molecular gene pathways, simultaneously. Thus, high-throughput gene array assay has the potential of identifying differential expression in genes encoding for various enzymes, kinases, ion channels, and other cell signaling molecules that determine individual's variation in response to drugs.

To address these issues, this study examined differences in gene expression in freshly isolated PBMCs isolated from GC-R and GC-S asthmatic patients, using high-density DNA microarray analysis. The results demonstrate that glucocorticoid sensitivity can be predicted with 86% accuracy.

It is widely accepted that glucocorticoids (GCs) are the most effective drugs available in asthma therapy. In individuals who are sensitive, inhaled GC has been shown to have a relatively low capacity to activate transcription within PBMCs at concentrations found in plasma and their action is thought to mainly occur within the lung. This finding is in agreement with the restricted systemic side effects at low or intermittent doses, whereas the relative abilities of GC to trans-repress transcription factor activities, such as AP-1 and NF-κB, in the airways is in agreement with their relative clinical efficacy. In contrast, GC-resistance has been defined by the lack of a response to a prolonged course of high dose (>1 mg/kg/day) oral glucocorticoid such as prednisone. Since most patients with asthma are being treated with inhaled GC, a new definition referring to GC-dependent/resistant asthma has emerged taking into account the inhalation route in the use of the drug (Leung, D. and Chrousos, G., Am. J. Resp. Crit. Care Med. 2000. 162:1–3). In light of these issues, a recommendation to define GC-resistant asthma as a condition where there is incomplete response to high doses of inhaled GC (i.e., >2,000 mg/day) was followed (Gagliardo, R. et al., Am. J. Resp. Crit. Care Med. 2000. 162:7–13). While clear separation between patients with high level of GC-dependent versus GC-resistant asthma is not always possible clinically, there is no doubt that both of these groups present a challenging clinical problem that is highly costly to the health care system. Sub-optimal responses to steroids often lead to prolonged courses of high-dose GC therapy accompanied by serious adverse effects together with persistent airway compromise. Patients with GC-resistant asthma present an ongoing inflammation of the airways despite persistent treatment with high doses of GC. This would be consistent with the high degree of airway hyperresponsiveness detected in our GC-R patients as reflected by the low methacholine concentration values in Table 3.

Given the pathobiologic processes involved in asthma, as a first approximation, it is reasonable to consider GC-insensitive and GC-dependent asthma as a part of the same pathogenic process. Thus, in view of potential heterogeneity and complexity of mechanisms contributing to GC-resistant/dependent asthma and its potential impact on the natural history of chronic asthma, it is noteworthy that no differences in the gene expression profiles of our GC-dependent study patients with moderate to severe GC-resistance, with respect to their GC resistant trait, were found.

In this study, a gene-scoring approach to identify genes that provide predictive power was used. As shown in Table 1, the 40 genes selected differed in their signal intensities of mRNA expression between the two groups and correlated strongly with the patients response phenotypes to inhaled glucocorticoids. Moreover, as shown in FIG. 1, when a Bayesian classifier was trained on a subset of 14 GC-S and 14 GC-R patients the predictive accuracy of the classifier to discriminate between these two patient groups was 82%. When the classifier was trained on 40, the accuracy of the classifier to predict the remaining independent patients was as high as 86% (FIG. 2). Thus, by almost doubling the number of patients that were used to train the classifier, the predictive power of the study increased further. The latter observation has two important implications: 1) it suggests that the predictive accuracy of the classifier might improve further if additional patients are included; and 2) the approach using the naïve Bayesian classifier when applied to the initial data set of 14 GC-S and 14 GC-R patients, provided sufficient power to predict gene expression profiles of GC-R and GC-S asthmatics with over 80% accuracy. It is noteworthy that among these genes are numerous cytokine/chemokine-related genes, transcription factors and cell signaling molecule genes (Tables 1, 2A and 2B). No doubt many of these genes may turn out to be critical regulatory genes of GC responsiveness independent of asthma per se.

Genes with predictive power in discriminating between glucocorticoid sensitive and glucocorticoid responsive asthmatics are listed in Table 1. The 40 genes that most accurately discriminate between glucocorticoid-responsive (GC-R) and glucocorticoid-sensitive (GC-S) asthmatics using fold change mRNA expression values following stimulation with cytokines are shown. The values expressed as mean±SEM for the groups. Also shown are comparable values in 14 non-asthmatic (control) subjects with unknown GC-response status. Expression profiles including these genes predict GC-R and GC-S patients with over 80% accuracy.

TABLE 1

Mean Fold change in RNA Expression of Informative Genes

| Gene Category | Name/ GenBank | GCR mean ± sem | GCS mean/± sem | Control mean/± sem | PV |
|---|---|---|---|---|---|
| Transcription Factors | | | | | |
| Zinc finger Protein 267 | ZNF267/X78925 | 3.05 ± 0.45 | 5.41 ± 0.99 | 3.76 ± 0.30 | 0.94 |
| Zinc finger Protein 189 | ZNF189/AF025770 | 2.98 ± 0.38 | 4.12 ± 0.61 | 2.92 ± 0.44 | 0.88 |
| Interferon-stimulated gene factor 3 | ISGF-3/M97935 | 1.50 ± 0.80 | 4.38 ± 0.78 | 2.28 ± 0.59 | 0.82 |
| N-myc and STAT interactor | Nmi/U32849 | 2.28 ± 0.25 | 1.41 ± 0.20 | 1.50 ± 0.09 | 0.81 |
| Zinc finger helicase | ZFH/U91543 | −1.39 ± 0.20 | −2.04 ± 0.11 | −1.25 ± 0.19 | 0.79 |
| Zinc finger Protein 145 | ZNF145/AF060568 | −3.23 ± 0.88 | −7.79 ± 2.59 | −5.94 ± 1.65 | 0.71 |
| Interferon-induced leucine zipper protein | IFP35/U72882 | 2.66 ± 0.39 | 3.56 ± 0.27 | 2.70 ± 0.30 | 0.69 |
| C terminal binding protein | CtBP/U37408 | −1.36 ± 0.20 | −1.73 ± 0.30 | −1.43 ± 0.09 | 0.64 |
| Cell signaling/metabolism | | | | | |
| PDGF receptor beta-like tumor suppressor | PRLTS/D37965 | 0.51 ± 0.41 | 2.99 ± 0.58 | 0.67 ± 0.48 | 0.94 |
| Sterol carrier protein-X; sterol carrier protein-2 | SCP-X; SCP-2/U11313 | −2.44 ± 0.20 | −1.61 ± 0.35 | −1.86 ± 0.11 | 0.94 |
| G protein-linked receptor gene | GPRG/L42324 | 4.14 ± 1.35 | 8.46 ± 3.50 | 3.85 ± 1.16 | 0.94 |
| Nuclear Factor kappa B subunit | NFkB/M58603 | 4.10 ± 0.26 | 2.68 ± 0.25 | 3.12 ± 0.19 | 0.93 |
| Allograft inflammatory factor 1 | AIF1/U49392 | −4.48 ± 0.49 | −2.24 ± 0.54 | −4.54 ± 0.50 | 0.88 |
| c-syn protooncogene | FYN/M14333 | 1.87 ± 0.09 | 1.55 ± 0.11 | 1.74 ± 0.04 | 0.86 |
| Small nuclear ribonucleoprotein polypeptide A | SNRPA/M60784 | −1.75 ± 0.10 | −3.76 ± 1.34 | −1.80 ± 0.09 | 0.86 |
| 2′5′ Oligoadenylate synthetase | none/M87434 | 2.69 ± 0.35 | 4.52 ± 0.59 | 2.56 ± 0.49 | 0.81 |
| Rab GTPase activating protein 1 | HSRANGAP1/X82260 | 2.42 ± 0.13 | 1.89 ± 0.25 | 1.94 ± 0.31 | 0.79 |
| Vasoactive intestinal peptide receptor 1 | VIPR1/X77777 | −3.76 ± 0.52 | −11.65 ± 2.37 | −6.24 ± 1.02 | 0.79 |
| NADH-ubiquinone dehydrogenase 51 kDa subunit | NDUFV1/AF053070 | −1.54 ± 0.10 | −1.89 ± 0.31 | −1.61 ± 0.16 | 0.79 |
| SH3BGR-like protein | SH3BGRL/AF042081 | −2.04 ± 0.20 | −1.22 ± 0.29 | −1.88 ± 0.09 | 0.75 |
| SRC Kinase associated phosphoprotein 55K | SKAP55/Y11215 | −6.59 ± 0.48 | −12.60 ± 2.29 | −13.36 ± 5.40 | 0.71 |
| Retinal short-chain dehydrogenase/reductase | retSDR1/AF061741 | −0.61 ± 0.36 | 0.24 ± 0.40 | 0.33 ± 0.70 | 0.71 |
| NAD (H)-specific isocitrate dehydrogenase g | none/Z68907 | −1.58 ± 0.05 | −1.67 ± 0.30 | −1.60 ± 0.06 | 0.71 |
| Lysosome-associated membrane glycoprotein | DCLAMP/AB013924 | 70.09 ± 11.70 | 128.82 ± 24.64 | 96.54 ± 13.97 | 0.69 |
| Aryl carbon receptor | AHR/L19872 | −1.96 ± 0.38 | −0.82 ± 0.37 | −0.24 ± 0.45 | 0.69 |
| Ser/Thr kinase 10 | lok/AB013924 | −1.49 ± 0.06 | −1.47 ± 0.23 | −1.60 ± 0.08 | 0.64 |
| Docking protein 2 | DOK2/AF034970 | −2.08 ± 0.09 | −2.24 ± 0.54 | −2.55 ± 0.16 | 0.64 |
| Ecto-5-prime-nucleotidase | CD73/X55740 | −2.38 ± 0.20 | −4.22 ± 0.89 | −3.16 ± 0.94 | 0.64 |
| Signal-induced proliferation-associated gene 1 | SIPA1/AB005666 | −1.68 ± 0.29 | −2.76 ± 0.51 | −1.85 ± 0.15 | 0.57 |
| Phospholipid Scramblease | hMmTRA 1b/AB006746 | 3.80 ± 0.52 | 6.66 ± 0.82 | 3.94 ± 0.44 | 0.56 |
| Misc | | | | | |
| Fc fragment of IgEalpha | FCRER1A/X06948 | −17.64 ± 1.55 | −10.44 ± 2.36 | −16.43 ± 4.08 | 0.94 |
| Histone stem-loop binding protein | SLBP/U75679 | 1.07 ± 0.17 | 1.21 ± 0.31 | 0.69 ± 0.36 | 0.94 |
| Interferon induced protein 56 | IFI56/M24594 | 10.63 ± 2.73 | 23.63 ± 3.73 | 10.09 ± 2.24 | 0.88 |

TABLE 1-continued

Mean Fold change in RNA Expression of Informative Genes

| Gene Category | Name/ GenBank | GCR mean ± sem | GCS mean/± sem | Control mean/± sem | PV |
|---|---|---|---|---|---|
| Neuropathy target esterase | NTE/AJ004832 | −1.42 ± 0.25 | −2.34 ± 0.13 | −1.37 ± 0.24 | 0.86 |
| Interferon induced protein 41 | IFP41/L22342 | 1.32 ± 1.32 | 2.38 ± 0.23 | 1.44 ± 0.34 | 0.75 |
| Poly A binding protein II | PAPB2/AF026029 | −1.36 ± 0.06 | −2.02 ± 0.24 | 0.68 ± 0.31 | 0.71 |
| Galectin 2 | Gal2/AL022315 | −56.71 ± 7.96 | −23.46 ± 5.90 | −44.87 ± 8.65 | 0.69 |
| Actin related protein complex 2/3 subunit 2 | ARPC2/U50531 | −2.79 ± 0.65 | −7.05 ± 1.37 | −3.25 ± 1.36 | 0.57 |
| CD1c Thymocyte antigen cDNA | CD1c/M28827 | −5.11 ± 0.62 | −3.56 ± 0.34 | −4.73 ± 0.74 | 0.56 |
| clone 24538 mRNA | none/AF055030 | 0.84 ± 0.28 | 1.52 ± 0.24 | 1.42 ± 0.11 | 0.94 |

Tables 2A and 2B include 45 genes that were either upregulated or downregulated by IL-1β/TNFα therapy and were reversed, at least in part, by pre-treatment with GC, and that most accurately predicted glucocorticoid sensitivity using expression values generated following treatment with cytokines. Table 2A shows expression levels in cells treated with IL-1β/TNFα in the presence of DEX and Table 2B shows expression levels of cells treated with IL-1β/TNFα alone.

TABLE 2A

Genes upregulated by IL-1β/TNFα and repressed by DEX
IL1/TNFα treatment: With DEX

| Gene Category | Name/ GenBank | GCR mean ± sem | GCS mean/± sem | P-value |
|---|---|---|---|---|
| Inflammatory cell regulators | | | | |
| Interferon-inducible 56 Kd | IFI56/ M24594 | −816 ± 91 | −1920 ± 240 | <0.0001 |
| Interleukin 1β | IL1B/ M15330 | −3792 ± 501 | 1605 ± 1339 | 0 |
| Interferon gamma treatment inducible mRNA | IFNIND/ M26683 | −12235 ± 955 | −5432 ± 1553 | 0 |
| CD6 antigen | CD6/ X60992 | −1128 ± 192 | 58 ± 265 | 0.001 |
| Interferon regulatory factor 7B | IRF7/ U53831 | −908 ± 91 | −876 ± 175 | 0.863 |
| TNFα receptor associated factor 1 | EB16/ U19261 | −2061 ± 185 | −1419 ± 109 | 0.0133 |
| TNFα receptor | CD120b/ M32315 | −3321 ± 520 | −1283 ± 407 | 0.006 |
| TNFα receptor superfamily | WSL/ Y09392 | −3321 ± 506 | −1591 ± 402 | 0.0185 |
| Leukocyte surface aminopeptidase N | CD13/ M22324 | −983 ± 122 | −247 ± 106 | 0 |
| Cytokine (GRO-γ) | SCYB3/ M36821 | −2135 ± 345 | −672 ± 59 | 0.001 |
| Interferon-inducible peptide (6–16) gene | 16-jun/ U22970 | −1233 ± 151 | −2094 ± 424 | 0.041 |
| Cytokine (GRO-β) | SCYB2/ M36820 | −2934 ± 374 | −1116 ± 384 | 0.003 |
| Interferon-β-2a | IL6/ X04430 | −7784 ± 683 | −4493 ± 788 | 0.002 |
| OX40 cell surface antigen | OX40/ S76792 | −600 ± 103 | −230 ± 47 | 0 |
| Monocyte/macrophage lg-related receptor | MIR10/ AF004231 | −626 ± 73 | −238 ± 57 | 0 |
| Small inducible cytokine subfamily C2 | SCYC2/ D63789 | −417 ± 80 | −118 ± 76 | 0.0156 |
| Interleukin-1 receptor antagonist | IL1RA/ X52015 | −10750 ± 966 | −5445 ± 1457 | 0.004 |
| Urokinase-type plasminogen receptor | CD87/ U09937 | −3834 ± 530 | −1504 ± 272 | 0.002 |

TABLE 2A-continued

Genes upregulated by IL-1β/TNFα and repressed by DEX
IL1/TNFα treatment: With DEX

| Gene Category | Name/GenBank | GCR mean ± sem | GCS mean/± sem | P-value |
|---|---|---|---|---|
| Activation mRNA | Act-2/J04130 | −4202 ± 494 | −1333 ± 572 | 0.001 |
| Macrophage migration inhibitory factor | MIF/L19686 | −1222 ± 383 | −170 ± 238 | 0.0365 |
| Monocyte secretory protein | JE/M28225 | −7380 ± 860 | −4302 ± 960 | 0.0331 |
| Interferon stimulated gene HEM45 | HEM45/U88964 | −1600 ± 367 | −424 ± 368 | 0.039 |
| Membrane glycoprotein 4F2 antigen heavy chain | CD98/J02939 | −687 ± 115 | −301 ± 124 | 0.0374 |
| Interferon induced protein p78 | p78/M33882 | −3547 ± 345 | −1491 ± 346 | 0 |
| CD44 isoform RC | CD44/AF098641 | −1886 ± 170 | −1019 ± 134 | 0.001 |
| Interferon-induced 17-kDa/15-kDa protein | ISG15/M13755 | −5244 ± 677 | −2526 ± 611 | 0.008 |
| Cell Signaling/Metabolism | | | | |
| Plasminogen activator-inhibitor 2 | PAI-2/Y00630 | −7538 ± 623 | −2683 ± 648 | <0.0001 |
| PROS-27 | PROS-27/X59417 | −2771 ± 318 | −361 ± 402 | 0 |
| Cyclin dependent kinase inhibitor 1A | p21/U03106 | −2463 ± 315 | −885 ± 151 | 0 |
| Lymphocyte G0/G1 switch gene | G0S2/M69199 | −3788 ± 420 | −1657 ± 275 | 0 |
| Hpast | HPAST/AF001434 | −1532 ± 187 | −675 ± 139 | 0.002 |
| Apoptosis inhibitor/AP homolog B (MIHB) | AP11/U37547 | −722 ± 315 | −342 ± 151 | 0.002 |
| Insulin induced protein 1 | INSIG1/U96876 | −2778 ± 273 | −1797 ± 204 | 0.0117 |
| pim-1 oncogene | pim-1/M16750 | −1937 ± 245 | −1197 ± 152 | 0.0205 |
| Cyclic AMP-responsive element modulator | CREM/S68134 | −2225 ± 238 | −1435 ± 149 | 0.0207 |
| Glucose transporter-like protein-lll | GLUT3/M20681 | −3564 ± 801 | −1422 ± 512 | 0.0366 |
| Human cyclooxygenase-2 | hCox-2/U04636 | −1731 ± 222 | −2333 ± 389 | 0.167 |
| CAM/ECM molecules | | | | |
| HB14 | CD83/Z11697 | −4434 ± 73 | −2492 ± 78 | 0 |
| Adhesion molecule ninjurin | NINJ1/U91512 | −1977 ± 315 | −472 ± 249 | 0.001 |
| Tissue inhibitor of metalloproteinases 1 | TIMP1/D11139 | −4723 ± 500 | −2237 ± 483 | 0.002 |
| Elastase specific proteinase inhibitor | ELAFIN/L10343 | −1448 ± 462 | −292 ± 199 | 0.0449 |
| Transcription Factors | | | | |
| Nef-associated factor 1β | Naf1beta/AJ011896 | −1523 ± 467 | 126 ± 512 | 0.0268 |
| Thyroid receptor interactor | TRIP 14/L40387 | −635 ± 67 | −798 ± 83 | 0.1357 |
| Basic helix-loop-helix transcription factor | Musculin/AF087036 | −1867 ± 177 | −1209 ± 116 | 0.006 |
| p50-NFκβ | P50-NF-kB/S76638 | −890 ± 174 | −321 ± 105 | 0.0122 |

TABLE 2B

Genes upregulated by IL-1/TNF-α and repressed by DEX
IL1/TNFα treatment: Without DEX

| Gene Category | Name/ GenBank | GCR mean ± sem | GCS mean/± sem | P-value |
|---|---|---|---|---|
| Inflammatory cell regulators | | | | |
| Interferon-inducible 56 Kd | IFI56/ M24594 | 1283 ± 215 | 3370 ± 372 | <0.0001 |
| Interleukin 1β | IL1B/ M15330 | 9905 ± 1021 | 595 ± 1430 | <0.0001 |
| Interferon gamma treatment inducible mRNA | IFNIND/ M26683 | 17349 ± 784 | 11063 ± 998 | <0.0001 |
| CD6 antigen | CD6/ X60992 | 2472 ± 179 | 806 ± 195 | <0.0001 |
| Interferon regulatory factor 7B | IRF7/ U53831 | 1413 ± 129 | 3074 ± 187 | <0.0001 |
| TNFα receptor associated factor 1 | EB16/ U19261 | 5191 ± 188 | 3643 ± 267 | 0 |
| TNFα receptor | CD120b/ M32315 | 6742 ± 513 | 3453 ± 877 | 0 |
| TNFα receptor superfamily | WSL/ Y09392 | 6560 ± 462 | 3452 ± 626 | 0 |
| Leukocyte surface aminopeptidase N | CD13/ M22324 | 2988 ± 304 | 1523 ± 184 | 0.001 |
| Cytokine (GRO-γ) | SCYB3/ M36821 | 3228 ± 392 | 1431 ± 284 | 0.001 |
| Interferon-inducible peptide (6–16) gene | 16-jun/ U22970 | 1870 ± 317 | 3656 ± 362 | 0.002 |
| Cytokine (GRO-β) | SCYB2/ M36820 | 5431 ± 653 | 2267 ± 509 | 0.002 |
| Interferon-β-2a | IL6/ X04430 | 12870 ± 630 | 9257 ± 863 | 0.002 |
| OX40 cell surface antigen | OX40/ S76792 | 1157 ± 88 | 588 ± 28 | 0.002 |
| Monocyte/macrophage lg-related receptor | MIR10/ AF004231 | 1492 ± 147 | 780 ± 157 | 0.003 |
| Small inducible cytokine subfamily C2 | SCYC2/ D63789 | 483 ± 115 | 28 ± 90 | 0.006 |
| Interleukin-1 receptor antagonist | IL1RA/ X52015 | 13395 ± 1481 | 8202 ± 1598 | 0.0168 |
| Urokinase-type plasminogen receptor | CD87/ U09937 | 4180 ± 663 | 2054 ± 414 | 0.0197 |
| Activation mRNA | Act-2/ J04130 | 8697 ± 1013 | 3900 ± 1860 | 0.026 |
| Macrophage migration inhibitory factor | MIF/ L19686 | 2250 ± 705 | 296 ± 356 | 0.0271 |
| Monocyte secretory protein | JE/ M28225 | 9970 ± 999 | 6785 ± 534 | 0.0369 |
| Interferon stimulated gene HEM45 | HEM45/ U88964 | 6801 ± 713 | 4768 ± 553 | 0.0474 |
| Membrane glycoprotein 4F2 antigen heavy chain | CD98/ J02939 | 3073 ± 194 | 2472 ± 243 | 0.0662 |
| Interferon induced protein p78 | p78/ M33882 | 7155 ± 826 | 5241 ± 503 | 0.0777 |
| CD44 isoform RC | CD44/ AF098641 | 3651 ± 264 | 3121 ± 195 | 0.0962 |
| Interferon-induced 17-kDa/15-kDa protein | ISG15/ M13755 | 8821 ± 1574 | 6128 ± 993 | 0.1801 |
| Cell Signaling/Metabolism | | | | |
| Plasminogen activator-inhibitor 2 | PAI-2/ Y00630 | 9427 ± 717 | 5832 ± 531 | 0.001 |
| PROS-27 | PROS-27/ X59417 | 5853 ± 316 | 3557 ± 443 | 0 |
| Cyclin dependent kinase inhibitor 1A | p21/ U03106 | 3544 ± 492 | 1975 ± 261 | 0.0123 |
| Lymphocyte G0/G1 switch gene | G0S2/ M69199 | 1403 ± 737 | 1347 ± 548 | 0.9539 |
| Hpast | HPAST/ AF001434 | 2370 ± 263 | 1545 ± 272 | 0.0418 |
| Apoptosis inhibitor/AP homolog B (MIHB) | AP11/ U37547 | 1826 ± 137 | 1885 ± 150 | 0.7754 |
| Insulin induced protein 1 | INSIG1/ U96876 | 4414 ± 353 | 3201 ± 285 | 0.0175 |
| pim-1 oncogene | pim-1/ M16750 | 2347 ± 411 | 1947 ± 511 | 0.5462 |

TABLE 2B-continued

Genes upregulated by IL-1/TNF-α and repressed by DEX
IL1/TNFα treatment: Without DEX

| Gene Category | Name/ GenBank | GCR mean ± sem | GCS mean/± sem | P-value |
|---|---|---|---|---|
| Cyclic AMP-responsive element modulator | CREM/ S68134 | 4875 ± 216 | 4613 ± 411 | 0.541 |
| Glucose transporter-like protein-lll | GLUT3/ M20681 | 5396 ± 930 | 2914 ± 713 | 0.0476 |
| Human cyclooxygenase-2 | hCox-2/ U04636 | 1735 ± 302 | 2683 ± 513 | 0.1195 |
| CAM/ECM molecules | | | | |
| HB14 | CD83/ Z11697 | 5991 ± 138 | 2892 ± 150 | <0.0001 |
| Adhesion molecule ninjurin | NINJ1/ U91512 | 4607 ± 401 | 2359 ± 264 | 0 |
| Tissue inhibitor of metalloproteinases 1 | TIMP1/ D11139 | 9451 ± 1006 | 5574 ± 611 | 0.005 |
| Elastase specific proteinase inhibitor | ELAFIN/ L10343 | 2744 ± 768 | 577 ± 174 | 0.0166 |
| Transcription Factors | | | | |
| Nef-associated factor 1β | Naf1beta/ AJ011896 | 6890 ± 505 | 3412 ± 314 | <0.0001 |
| Thyroid receptor interactor | TRIP14/ L40387 | 1046 ± 130 | 1488 ± 167 | 0.0452 |
| Basic helix-loop-helix transcription factor | Musculin/ AF087036 | 2832 ± 297 | 2145 ± 109 | 0.0489 |
| p50-NFκβ | P50-NF-kB/ S76638 | 2394 ± 169 | 1995 ± 206 | 0.1487 |

As shown in Table 3, the ratio of males/females and the atopy status were lower in the GC-R group, whereas the mean age was higher. While several studies have reported association between the X chromosome and the asthma phenotype (Kauppi P. et al., *Eur. J. Hum. Genet.* 2000. 10:788–92; Heinzmann A. et al., *Hum. Mol. Genet.* 2000. 9:549–59; Ahmed S. et al., *Exp. Clin. Immunogenet.* 2000. 17:18–22), extended epidemiological studies are needed to confirm if such an association exists between the GC-R phenotype and asthma. Likewise, 54% of the GC-S patients in this study were skin test positive to one or more aeroallergens compared to 31% of the GC-R patients. In addition, the average total IgE levels were higher in the GC-S group. About 70% of patients in some European countries and areas of the United States are atopic (Eggleston P. and Bush R., *J. Allergy Clin. Immunol.* 2001 107:S403–5) compared to about 50% of asthmatics in Iceland, as determined by positive skin tests or elevated IgE levels (The European Community Respiratory Health Survey Group. *Am. J. Resp. Crit. Care Med.* 1997. 156:1773–1780). Whether atopic asthmatic patients are less likely to have GC-R asthma compared to non-atopic patients remains to be determined. While interference from these variables on the results cannot be excluded, the predictive power of the patient's age, sex or atopy status was lower (and not statistically significant) when compared to the power developed from the genes under study.

These results provide the basis for unraveling the mechanisms that contribute to the development of GC-resistance, and can allow for the development of new therapeutic approaches. For example, one of skill in the art can perform linkage studies on patients for GC-R and GC-S clusters using the Icelandic Genealogy Database. By linking patients with GC-R and GC-S asthma into large family pedigrees based on clinical measures of GC-responsiveness, a genome-wide linkage analysis can be performed. Secondly, by searching for mRNAs expression profiles that predict GC-R versus GC-S asthma in a larger cohort of patients using DNA array technology, one of skill in the art can categorize patients with unknown GC profile into GC-S and GC-R patients with high accuracy independent of whether the patient has been taking glucocorticoids or whether the clinical response has been determined based on the expression profile alone (e.g., if similar to the expression profiling of responders versus non-responders, respectively).

Table 3. Demographic, lung function, metacholine challenge and total IgE values in glucocorticoid-sensitive (GC-S) and GC-resistant(R) patients. Values expressed are mean+/−SE for the groups.

TABLE 3

| Characteristics | GC-S | <Asthma> | GC-R |
|---|---|---|---|
| n | 61 | | 35 |
| Mean age (yr) | 43 ± 16 | | 54 ± 19 |
| Sex ratio (M/F) | 30/70 | | 20/80 |
| Mean dose GC (μg/day) | 450 (200–800) | | 1,610 (1,000–2000) |
| FVC (% predicted) | 84 ± 19 | | 75 ± 15 |
| liters | 3.8 ± 1.0 | | 2.2 ± 0.8 |
| FEV1 (% predicted) | 82 ± 20 | | 81 ± 8 |
| liters | 3.2 ± 1.0 | | 3.3 ± 0.3 |
| FEV1/FVC ratio | 70 ± 10 | | 72 ± 12 |
| Positive skin tests | 54% | | 31% |
| MCh challenge (mg/L) | 3.4 ± 1.2 | | 0.7 ± 1.1 |
| Total IgE (IU/L) | 78 | | 38 |

To ensure that the gene signals that most accurately discriminate GC responders from non-responders are captured, the study was expanded to include 96 patients (60

GC-S and 36 GC-R) and randomly split cohorts of GC-S and GC-R patients with and without cross validation were analyzed.

The results demonstrate that apart from genes listed in Tables 1, 2A and 2B, 15 additional genes, listed in Table 4A, were identified with the split cohort method and 4 genes, listed in Table 4B, by the cross validation method, which increased the predictive accuracy to 86% and 89% for the independent set and cross validation method, respectively. These genes play a key role in immune function, signal transduction processes and in apoptosis, all of which are highly relevant functions to the mechanisms of glucocorticoid responsiveness in asthma.

TABLE 4A

| Induction Independent GenBank | Mean Resistant | Std Dev | Mean Sensitive | Std Dev |
|---|---|---|---|---|
| Z11697 | 1.8724782 | 0.33308947 | 1.58067 | 0.37548256 |
| AI950382 | 1.3549194 | 0.22042978 | 1.030298 | 0.2444671 |
| L78440 | 1.5259613 | 0.30956995 | 1.0863237 | 0.34783307 |
| U19261 | 1.7525064 | 0.4171106 | 1.3473015 | 0.3836438 |
| M80244 | 1.9161059 | 0.56795007 | 1.1932454 | 0.40928963 |
| AB023205 | 2.1412642 | 0.9683697 | 1.55956 | 0.7753593 |
| M58603 | 1.6857204 | 0.40931362 | 1.2413435 | 0.41113004 |
| L05424 | 1.8005482 | 0.49951264 | 1.3440721 | 0.3783 |
| R38263 | 1.4709008 | 0.3948905 | 1.2489537 | 0.32604253 |
| L03411 | 1.2816724 | 0.18822539 | 1.1264083 | 0.25873253 |
| D63789 | 1.6949914 | 0.78736067 | 1.2824732 | 0.57320374 |
| X52425 | 1.4263631 | 0.3121133 | 1.1701844 | 0.32265002 |
| L11329 | 1.6712576 | 0.45524144 | 1.2668103 | 0.39379898 |

TABLE 4A-continued

| Induction Independent GenBank | Mean Resistant | Std Dev | Mean Sensitive | Std Dev |
|---|---|---|---|---|
| U48807 | 2.149289 | 1.1046098 | 1.4393674 | 0.74329394 |
| D79991 | 1.2781677 | 0.26072037 | 1.1245298 | 0.2646311 |

TABLE 4B

| Induction Cross Validation GenBank | Mean Resistant | StdDev | Mean Sensitive | StdDev |
|---|---|---|---|---|
| AB009010 | 0.7325509 | 0.3312249 | 1.4231814 | 0.5362498 |
| L78440 | 1.575848 | 0.33741876 | 1.1237841 | 0.30317423 |
| U43185 | 2.1323266 | 0.40701827 | 1.4901624 | 0.52416813 |
| AB020630 | 1.6486217 | 0.2412822 | 1.2882963 | 0.31817988 |

Example 2

Apart from genes that demonstrated predictive accuracy in the around 80%, a large number of genes were found to be differentially expressed between the two patient groups. Of those, the genes listed in Tables 5A–E contributed to the predictive signal that was found. These genes were identified by applying the biological approach of the experimental set up (i.e., genes upregulated or downregulated by IL-1β/TNFα and reversed, at least in part by GC). The ultimate value of the genes in Tables 5A–5E with respect to glucocorticoid prediction will be known when these genes have been validated in a larger cohort of patients.

TABLE 5A

| | BASELINE EXPRESSION VALUES | | | | |
|---|---|---|---|---|---|
| | GC resistant (n = 30) | | GC sensitive (n = 66) | | |
| Gene (Genbank, Map) | MEAN | SEM | MEAN | SEM | P value |
| Perforin 1 (M28393, 10q22) | 6085.97 | 417.13412 | 5250.672 | 208.2762 | 0.026 |
| Tumor necrosis factor receptor 2 (75 kD) (M32315, 1p36.3–p36.2) | 4043.2695 | 172.13469 | 3606.906 | 126.01189 | 0.047 |
| LPS-induced TNF-alpha factor (AF010312, 16p13.3–p12) | 4149.5264 | 339.81314 | 3394.3865 | 152.35988 | 0.018 |
| Defensin (L12691, 8) | 15084.323 | 1903.8826 | 10559.057 | 1213.1726 | 0.045 |
| KIAA0542 protein (AB011114, 22q12.2) | 4974.1274 | 1201.7789 | 8108.8516 | 872.0196 | 0.004 |
| Beta 2-microglobulin (S82297, 15q21–q22.2) | 14026.682 | 3886.1045 | 28540.09 | 3071.3684 | 0.023 |
| Granzyme B precursor (M57888, 14q11.2) | 3153.3257 | 372.53757 | 2298.1396 | 185.16092 | 0.01 |
| Thymosin, beta 4 (M17733, Xq21.3–q22) | 21235.469 | 2459.579 | 28695.383 | 2114.4946 | 0.042 |
| HLA class I heavy chain (X58536, 6p21.3) | 23571.922 | 2747.8547 | 31607.03 | 2214.8435 | 0.042 |
| Elongation factor EF-1-alpha (J04617, 6q14) | 18835.99 | 3337.1677 | 30409.002 | 2609.5315 | 0.034 |
| EST (AI526078, 20q13.3) | 18714.736 | 1704.359 | 24808.363 | 1547.6501 | 0.043 |
| CD98 (M80244, 16q24.3) | 798.8602 | 93.80168 | 642.308 | 47.76093 | ns** |
| Nuclear factor kappa-B DNA binding subunit (M58603, 4q24) | 1118.8152 | 131.4039 | 1171.212 | 94.15151 | ns** |

TABLE 5A-continued

| | BASELINE EXPRESSION VALUES | | | | |
|---|---|---|---|---|---|
| | GC resistant (n = 30) | | GC sensitive (n = 66) | | |
| Gene (Genbank, Map) | MEAN | SEM | MEAN | SEM | P value |
| Signal transducer and activator of transcription 4 (L78440, 2q32.2–q32.3) | 2115.2861 | 177.11328 | 2072.295 | 94.97464 | ns** |
| Nef-associated factor 1 (AJ011896, 5q32–q33.1) | 2744.2788 | 242.81891 | 2588.429 | 162.65399 | ns** |
| CD44 antigen (L05424, 11p13) | 1856.1018 | 95.87001 | 1778.6385 | 104.54533 | ns** |
| (2'–5')oligoadenylate synthetase (AJ225089, 12q24.2) | 337.42038 | 18.820648 | 383.4079 | 54.559353 | ns** |
| Interferon regulatory factor 7 isoform a (U53831, 11p15.5) | 820.22296 | 40.891983 | 803.94714 | 37.65985 | ns** |
| Interferon-inducible protein p78 (M33882, 21q22.3) | 692.43274 | 53.86486 | 769.75037 | 61.446373 | ns** |
| interferon inducible 1-8U gene (X57352, 11) | 10073.882 | 1202.4331 | 10348.615 | 847.59143 | ns** |
| Interferon stimulated gene (20 kD) (U88964, 15q26) | 2559.649 | 120.11462 | 2733.2332 | 64.77266 | ns** |
| Interferon-stimulated protein, 15 kDa (m13755, 1) | 2001.0354 | 107.30703 | 2131.9282 | 121.11149 | ns** |
| CD44 isoform RC (AF098641, 11p13) | 1635.3041 | 92.87121 | 1546.3922 | 101.99627 | ns** |
| CD83 antigen (Z11697, 6p23) | 4003.7795 | 509.4784 | 2995.624 | 343.3428 | ns** |
| Interferon stimulatable response element (U22970, 1p36) | 1222.6351 | 87.984886 | 1198.6647 | 74.25269 | ns** |
| TNF receptor-associated factor 1 (U19621, 9q33–q34) | 1024.6047 | 76.8937 | 970.14984 | 68.22721 | ns** |
| Adhesion molecule ninjurin 1 (U01512, 9q22) | 952.9832 | 108.31899 | 819.72675 | 72.15633 | ns** |
| TNF receptor-associated factor 1 (U19261, 9q33–q34) | 602.10754 | 55.548782 | 552.6948 | 36.47862 | ns** |
| Transcription factor ISGF-3 (M97936, 2q32.2) | 1047.2883 | 84.6747 | 1043.8727 | 51.559406 | ns** |
| interleukin-7 receptor (AF043129, 5p13) | 1293.5005 | 221.00233 | 1776.9689 | 196.31573 | ns** |
| Interleukin 8 (M28130, 4q13–q21) | 9098.902 | 881.07416 | 7048.5723 | 759.5493 | ns** |
| GRO2 oncogene (M36820, 4q21) | 3172.951 | 401.67627 | 2370.0527 | 298.47812 | ns** |
| Interferon-induced protein with tetratricopeptide repeats 1 M24594, 10q25–q26) | 242.70598 | 46.875942 | 299.46494 | 47.465668 | ns** |
| interferon-induced protein with tetratricopeptide repeats 4 (AF026939, 10q24) | 335.2246 | 98.50067 | 348.74557 | 38.996685 | ns** |
| Macrophage colony stimulating factor 1 (M37435, 1p21–p13) | 3976.1692 | 148.23972 | 4297.3677 | 118.11726 | ns** |
| Ras inhibitor (M37190, 20) | 103.64886 | 51.292507 | 117.76897 | 47.070602 | ns** |
| Small inducible cytokine A2 (M28225, 17q11.2–q21.2) | 176.61205 | 47.855843 | 356.2777 | 170.02516 | ns** |
| Cyclooxygenase-2 (U04636, 1q25.2–q25.3) | 1282.8784 | 245.26799 | 976.03503 | 140.18762 | ns** |
| Transforming growth factor, beta receptor II (70–80 kD) (D50683, 3p22) | 665.96454 | 39.320732 | 684.6929 | 31.560013 | ns** |

TABLE 5A-continued

| | BASELINE EXPRESSION VALUES | | | | |
|---|---|---|---|---|---|
| | GC resistant (n = 30) | | GC sensitive (n = 66) | | |
| Gene (Genbank, Map) | MEAN | SEM | MEAN | SEM | P value |
| Cyclic AMP-responsive element modulator beta isoform (S68134, 10p12.2–p11.1) | 571.4737 | 76.16772 | 583.9707 | 86.563515 | ns** |
| Interleukin 1 receptor antagonist (X52015, 2q14.2) | 2650.151 | 386.6683 | 2049.2832 | 280.7141 | ns** |
| Interleukin 6 (X04430, 7p21) | 218.93637 | 79.35666 | 372.81815 | 181.83186 | ns** |
| Nef-associated factor 1 (AJ011896, 5q32–q33.1) | 1628.6475 | 86.34723 | 1530.4146 | 92.62164 | ns** |
| Small inducible cytokine A7 (X72308, 17q11.2–q12) | 121.53884 | 8.26777 | 149.0766 | 20.418268 | ns** |
| Small inducible cytokine A2 (M26683, 17q11.2–q21.1) | 227.42393 | 82.810646 | 527.6503 | 265.94244 | ns** |

TABLE 5B

| | IL-1/TNF-INDUCED EXPRESSION VALUES | | | | |
|---|---|---|---|---|---|
| | GC resistant (n = 30) | | GC sensitive (n = 66) | | |
| Gene | MEAN | SEM | MEAN | SEM | P value |
| Perforin 1 | 5614.334 | 394.1253 | 4072.83 | 214.3326 | <0.0001 |
| Tumor necrosis factor receptor 2 (75 kD) (M32315, 1p36.3–p36.2) | 10050.87 | 586.6837 | 7283.63 | 440.3941 | 0.0004 |
| LPS-induced TNF-alpha factor (AF010312, 16p13.3–p12) | 5459.401 | 351.0782 | 4387.12 | 170.5484 | 0.001 |
| Defensin (L12691, 8) | 8846.362 | 1376.016 | 4290.63 | 844.5093 | 0.009 |
| KIAA0542 protein (AB01114, 22q12.2) | 2017.074 | 946.1356 | 8857.14 | 1124.027 | 0.01 |
| Beta 2-microglobulin (S82297, 15q21–q22.2) | 6333.009 | 3069.832 | 28707 | 3191.635 | 0.01 |
| Granzyme B precursor (m57888, 14q11.2) | 1746.806 | 232.9423 | 957.865 | 111.5382 | 0.016 |
| Thymosin, beta 4 (m17733, Xq21.3–q22) | 18450.77 | 2309.75 | 31440.1 | 2229.507 | 0.02 |
| HLA class I heavy chain (X58536, 6p21.3) | 17262.1 | 2654.092 | 34519.5 | 2601.363 | 0.02 |
| Elongation factor EF-1-alpha (J04617, 6q14) | 15154.59 | 2826.921 | 35443.6 | 2869.217 | 0.03 |
| EST (AI526078, 20q13.3) | 15054.68 | 1528.611 | 25434.4 | 1606.93 | 0.03 |
| CD98 (M80244, 16q24.3) | 5682.373 | 365.3485 | 4127.05 | 234.5741 | <0.0001 |
| Nuclear factor kappa-B DNA binding subunit (M58603, 4q24) | 7222.51 | 338.3345 | 5655.56 | 215.4376 | <0.0001 |
| Signal transducer and activator of transcription 4 (178440, 2q32.2–q32.3) | 7142.53 | 347.9236 | 5567.9 | 216.9498 | <0.0001 |
| Nef-associated factor 1 (AJ011896, 5q32.q33.1) | 10042.95 | 525.3091 | 8829.79 | 312.5778 | <0.0001 |
| CD44 antigen (L05424, 11p13) | 6209.805 | 263.4941 | 5019.8 | 163.5661 | <0.0001 |
| (2′–5′)oligoadenylate synthetase (AJ225089, 12q24.2) | 3611.673 | 259.3965 | 1756.89 | 225.7237 | <0.0001 |
| Interferon regulatory factor 7 isoform a (U53831, 11p15.5) | 2841.19 | 237.6626 | 1681.36 | 160.3967 | <0.0001 |
| Interferon-inducible protein p78 (M33882, 21q22.3) | 4426.94 | 533.6766 | 1780.97 | 325.196 | <0.0001 |

TABLE 5B-continued

| | IL-1/TNF-INDUCED EXPRESSION VALUES | | | | |
|---|---|---|---|---|---|
| | GC resistant (n = 30) | | GC sensitive (n = 66) | | |
| Gene | MEAN | SEM | MEAN | SEM | P value |
| interferon inducible 1-8U gene (X57352, 11) | 5763.147 | 1332.153 | 4255.33 | 398.2605 | <0.0001 |
| Interferon stimulated gene (20 kD) (U88964, 15q26) | 6082.724 | 624.8853 | 4290.37 | 330.7253 | <0.0001 |
| Interferon-stimulated protein, 15 kDa (M13755, 1) | 10922.46 | 1395.841 | 4956.73 | 622.4254 | <0.0001 |
| CD44 isoform RC (AF09861, 11p13) | 5146.13 | 287.7974 | 3879.53 | 144.6777 | <0.0001 |
| CD83 antigen (Z11697, 6p23) | 9242.953 | 350.8769 | 7918.24 | 339.6289 | <0.0001 |
| Interferon stimulatable response element (U22970, 1p36) | 3203.982 | 495.8736 | 1631.66 | 281.1401 | 0.0001 |
| TNF receptor-associated factor 1 (U19261, 9q33–q34) | 5005.59 | 208.4321 | 4098.21 | 179.4619 | 0.0002 |
| Adhesion molecule ninjurin 1 (U91512, 9q22) | 3715.181 | 268.8716 | 3157.01 | 122.5063 | 0.0003 |
| TNF receptor-associated factor 1 (U19261, 9q33–q34) | 2364.498 | 96.09024 | 2096.81 | 78.13522 | 0.0007 |
| Transcription factor ISGF-3 (M97936, 2q32.2) | 1760.116 | 279.2687 | 1217.01 | 143.1016 | 0.014 |
| interleukin-7 receptor (AF043129, 5p13) | 2027.312 | 184.3109 | 2307.75 | 174.5007 | 0.02 |
| Interleukin 8 (M28130, 4q13–q21) | 13608.48 | 1609.251 | 17969.3 | 1448.031 | 0.02 |
| GRO2 oncogene (M35820, 4q21) | 6961.234 | 707.7638 | 5737.08 | 415.0885 | 0.001 |
| Interferon-induced protein with tetratricopeptide repeats 1 (M24594, 10q25–q26) | 1572.879 | 319.6902 | 713.604 | 178.921 | 0.009 |
| interferon-induced protein with tetratricopeptide repeats 4 (AF026939, 10q24) | 1759.121 | 304.6315 | 828.759 | 214.6707 | 0.005 |
| Macrophage colony stimulating factor 1 (m37435, 1p21–p13) | 3364.842 | 117.2874 | 4029.78 | 110.6731 | 0.04 |
| Ras inhibitor (m37190, 20) | 1611.356 | 177.1993 | 860.944 | 120.8235 | 0.0003 |
| Small inducible cytokine A2 (M28225, 17q11.2–q21.1) | 10048.81 | 755.9874 | 8072.22 | 495.8341 | 0.007 |
| Cyclooxygenase-2 U04636, 1q25.2–q25.3) | 3765.675 | 255.1504 | 2568.34 | 233.2174 | <0.0001 |
| Transforming growth factor, beta receptor II (70–80 kD) (D50683, 3p22) | 740.8099 | 79.60563 | 844.935 | 86.39076 | 0.04 |
| Cyclic AMP-responsive element modulator beta isoform (S681634, 10p12.1–p11.1) | 6531.873 | 386.0808 | 5686.2 | 268.2961 | 0.017 |
| Interleukin 1 receptor antagonist (X52015, 2q14.2) | 13211.16 | 1126.502 | 9535.15 | 642.7608 | <0.0001 |
| Interleukin 6 (X04430, 7p21) | 13482.49 | 852.9056 | 10099.2 | 625.5049 | <0.0001 |
| Nef-associated factor 1 (AJ011896, 5q32–q33.1) | 5100.91 | 671.4467 | 4788.67 | 294.8366 | 0.004 |
| Small inducible cytokine A7 (X72308, 17q11.2–q12) | 766.0895 | 165.4574 | 686.035 | 91.85867 | 0.02 |
| Small inducible cytokine A2 (M26683, 17q11.2–q21.1) | 17108.01 | 1043.492 | 12566.7 | 742.7468 | 0.003 |

TABLE 5C

| | L-1/TNF-INDUCED EXPRESSION VALUES WITH GC | | | | |
|---|---|---|---|---|---|
| | GC resistant (n = 30) | | GC sensitive (n = 66) | | |
| Gene (Genbank, Map) | MEAN | SEM | MEAN | SEM | P value |
| Perforin 1 (M28393, 10q22) | 5932.6836 | 324.4973 | 4613.415 | 214.7653 | 0.0007 |
| Tumor necrosis factor receptor 2 (75 kD) (M32315, 1p36.3–p36.2) | 7508.2896 | 451.0622 | 6416.635 | 365.9207 | 0.0731 |
| LPS-induced TNF-alpha factor (AF010312, 16p13.3–p12) | 5786.222 | 306.7707 | 4946.478 | 171.3137 | 0.0127 |
| Defensin (L12691, 8) | 11441.772 | 1372.689 | 7818.661 | 922.0382 | 0.0251 |
| KIAA0542 protein (AB011114, 22q12.2) | 5714.3643 | 1558.592 | 9333.106 | 1256.301 | 0.0201 |
| Beta 2-microglobulin (S82297, 15q21–q22.2) | 13301.895 | 2780.221 | 30811.06 | 3742.183 | 0.0027 |
| Granzyme B precursor (M57888, 14q11.2) | 1877.4227 | 216.4729 | 1227.949 | 107.5656 | 0.003 |
| Thymosin, beta 4 (M17733, Xq21.3–q22) | 19120.795 | 1911.539 | 26315.6 | 1943.828 | 0.019 |
| HLA class I heavy chain (X58536, 6p21.3) | 22299.861 | 2913.894 | 34067.19 | 3096.341 | 0.0145 |
| Elongation factor EF-1-alpha (J04617, 6q14) | 18670.865 | 3364.731 | 33042.49 | 3553.801 | 0.0015 |
| EST (AI526078, 20q13.3) | 17650.287 | 1587.158 | 25903.59 | 1771.242 | 0.0032 |
| CD98 (M80244, 16q24.3) | 5768.97 | 406.1578 | 4463.957 | 177.7024 | 0.0011 |
| Nuclear factor kappa-B DNA binding subunit (M58603, 4q24) | 6144.28 | 307.2589 | 5010.971 | 179.1457 | 0.0012 |
| Signal transducer and activator of transcription 4 (L78440, 2q32.2–q32.3) | 6800.764 | 284.0342 | 5744.643 | 184.6763 | 0.0021 |
| Nef-associated factor 1 (AJ011896, 5q32–q33.1) | 9655.332 | 495.7066 | 8075.491 | 259.7791 | 0.0026 |
| CD44 antigen (L05424, 11p13) | 4486.082 | 168.28 | 3818.656 | 133.3167 | 0.0042 |
| (2'–5')oligoadenylate synthetase (AJ225089, 12q24.2) | 1667.9843 | 164.3503 | 1064.525 | 130.1923 | 0.0054 |
| Interferon regulatory factor 7 isoform a (U53831, 11p15.5) | 2292.962 | 205.8358 | 1611.122 | 146.0624 | 0.007 |
| Interferon-inducible protein p78 (M33882, 21q22.3) | 2946.7205 | 383.2516 | 1801.234 | 251.7923 | 0.0099 |
| interferon inducible 1-8U gene (X57352, 11) | 8983.514 | 1053.469 | 6070.849 | 616.6636 | 0.0109 |
| Interferon stimulated gene (20 kD) (U88964, 15q26) | 6519.748 | 401.4738 | 5387.727 | 239.7823 | 0.012 |
| Interferon-stimulated protein, 15 kDa (m13755, 1) | 6071.2886 | 915.0679 | 3757.143 | 548.3279 | 0.021 |
| CD44 isoform RC (AF098641, 11p13) | 3719.6047 | 178.2906 | 3236.746 | 115.0394 | 0.0225 |
| CD83 antigen (Z11697, 6p23) | 4931.093 | 295.5049 | 4274.713 | 230.1791 | 0.0354 |
| Interferon stimulatable response element (U22970, 1p36) | 2737.275 | 346.7752 | 1615.407 | 174.2281 | 0.011 |
| TNF receptor-associated factor 1 (U19621, 9q33–q34) | 3581.1409 | 185.2364 | 2935.34 | 116.3565 | 0.0027 |
| Adhesion molecule ninjurin 1 (U01512, 9q22) | 3173.9238 | 222.309 | 2405.162 | 110.9695 | 0.0008 |
| TNF receptor-associated factor 1 (U19261, 9q33–q34) | 1790.2013 | 89.11578 | 1506.127 | 60.22232 | 0.0085 |
| Transcription factor ISGF-3 (M97936, 2q32.2) | 1490.314 | 178.5814 | 1048.989 | 102.7824 | 0.0212 |
| interleukin-7 receptor (AF043129, 5p13) | 3344.87 | 271.804 | 4565.661 | 279.8599 | 0.0057 |
| Interleukin 8 (M28130, 4q13–q21) | 12848.457 | 926.3713 | 14222.37 | 992.1271 | ns** |
| GRO2 oncogene (M36820, 4q21) | 5052.562 | 564.9373 | 4225.244 | 349.2652 | ns** |

TABLE 5C-continued

| | L-1/TNF-INDUCED EXPRESSION VALUES WITH GC | | | | |
|---|---|---|---|---|---|
| | GC resistant (n = 30) | | GC sensitive (n = 66) | | |
| Gene (Genbank, Map) | MEAN | SEM | MEAN | SEM | P value |
| Interferon-induced protein with tetratricopeptide repeats 1 (M24594, 10q25–q26) | 1094.8508 | 209.4019 | 672.1904 | 127.6253 | ns** |
| interferon-induced protein with tetratricopeptide repeats 4 (AF026939, 10q24) | 1109.5538 | 162.5891 | 743.2253 | 123.5186 | ns** |
| Macrophage colony stimulating factor 1 (M37435, 1p21–p13) | 3624.9211 | 172.8444 | 3983.53 | 132.856 | ns** |
| Ras inhibitor (M37190, 20) | 1615.0812 | 183.4838 | 1285.366 | 118.4882 | ns** |
| Small inducible cytokine A2 (M28225, 17q11.2–q21.2) | 3485.5967 | 409.9117 | 2908.787 | 418.8578 | ns** |
| Cyclooxygenase-2 (U04636, 1q25.2–q25.3) | 1004.8341 | 151.2995 | 1012.272 | 148.0441 | ns** |
| Transforming growth factor, beta receptor II (70–80 kD) (D50683, 3p22) | 998.71014 | 94.93384 | 1135.562 | 93.18079 | ns** |
| Cyclic AMP-responsive element modulator beta isoform (S68134, 10p12.2–p11.1) | 4027.2566 | 290.9312 | 4019.365 | 190.1472 | ns** |
| Interleukin 1 receptor antagonist (X52015, 2q14.2) | 4454.89 | 509.2246 | 3887.395 | 543.3725 | ns** |
| Interleukin 6 (X04430, 7p21) | 6479.466 | 737.0165 | 5473.95 | 617.1881 | ns** |
| Nef-associated factor 1 (AJ011896, 5q32–q33.1) | 5710.245 | 619.1145 | 5202.576 | 322.5588 | ns** |
| Small inducible cytokine A7 (X72308, 17q11.2–q12) | 283.77304 | 23.31367 | 334.6954 | 61.4575 | ns** |
| Small inducible cytokine A2 (M26683, 17q11.2–q21.1) | 5850.6055 | 630.0103 | 4954.649 | 646.567 | ns** |

TABLE 5D

| Genbank | SET1/2 Systematic | Common | Description | Map |
|---|---|---|---|---|
| AL049963 | 40456_at | | Source: *Homo sapiens* mRNA; cDNA DKFZp564A132 (from clone DKFZp564A132) | 4 |
| S68134 | 32066_g_at | CREM | CREM-β | 10p12.1–p11.1 |
| M58603 | 1378_g_at | KBF1 | Human nuclear factor kappa-B DNA binding subunit (NF-kβ) mRNA, complete cds | 4q24 |
| M13755 | 1107_s_at | ISG15 | 17-kDa protein | 1 |
| L31584 | 1097_s_at | EBI1 BLR2 CMKBR7 | Source: Human G-protein-coupled receptor (EBI 1) gene exon 3 | 17q12–q21.2 |
| AF022375 | 36100_at | VEGFA | *H. sapiens* vascular endothelial growth factor mRNA, complete cds. | 6p12 |
| M58603 | 1377_at | KBF1 | Human nuclear factor kappa-B DNA binding subunit (NF-kβ) mRNA, complete cds | 4q24 |
| M58603 | 38438_at | KBF1 | Human nuclear factor kappa-B DNA binding subunit (NF-κβ) mRNA, complete cds | 4q24 |

TABLE 5D-continued

| Genbank | SET1/2 Systematic | Common | Description | Map |
|---|---|---|---|---|
| U88964 | 33304_at | HEM45 | low level estrogen-modulated; deduced ORF detected by anti-peptide antisera | 15q26 |
| L08177 | 931_at | EBI2 | Epstein-Barr virus induced gene 2 (lymphocyte-specific G protein-coupled receptor) | 13 |
| D67031 | 33102_at | ADDL | Source: $H.$ $sapiens$ ADDL mRNA for adducin-like protein, complete cds. | 10q24.2–q24.3 |
| AL021977 | 36711_at | HS5O6A DKFZP586A1024 | C22orf5 | 22q12 |
| V01512 | 1916_s_at | c-fos | Source: Human cellular oncogene c-fos (complete sequence). | 14q24.3 |
| X59417 | 36122_at | IOTA PROS27 | Source: $H.sapiens$ PROS-27 mRNA | 14q13 |
| | HH BASELINE Rest ()*S | | | |
| X02910 | 1852_at | TNFA DIF TNFSF2 | Tumor necros factor | 6p21.3 |
| M15330 | 39402_at | IL1B | Source: Human interleukin 1-β (IL1B) mRNA, complete cds | 2q14 |
| J04130 | 36674_at | MIP-1-BETA | SCYA4, MIP1B | 17q21 |
| M28130 | 1369_s_at | IL8 | Source: Human interleukin 8 (IL8) gene, complete cds | 4q13–q21 |
| D90144 | 36103_at | MIPA SCYA3 | MIP1A | 17q11–q21 |
| S81914 | 1237_at | IEX-1 | radiation-inducible immediate-early gene | 6p21.3 |
| L11329 | 1292_at | PAC-1 PAC1 | PAC-1; putative | 2q11 |
| M57888 | 32370_at | CSPB CTLA1 CCPI CGL-1 CSP-B | Source: Human (clone lambda B34) cytotoxic T-lymphocyte-associated serine esterase 1 (CTLA1) gene complete cds | 14q11.2 |
| M16441 | 259_s_at | TNFSF1 TNFB LT | lymphotoxin | 6p21.3 |
| X68277 | 1005_at | CL 100 | Source: $H.$ $sapiens$ CL 100 mRNA for protein tyrosine phosphatase | 5q34 |
| X78992 | 32588_s_at | ERF2 TIS11D | Source: $H.$ $sapiens$ ERF-2 mRNA | 2 |
| L12691 | 31506_s_at | DEF3 HNP-3 | defensin | 8 |
| Z11697 | 37536_at | CD83 | a cell-surface molecule expressed by interdigitating reticulum cells, Langerhans cells and activated lymphocytes. A member of immunoglobin superfamily | 6p23 |
| M69199 | 38326_at | G0S2 | Source: Human G0S2 protein gene, complete cds | 1q32.2–q41 |
| M17017 | 35372_r_at | MDNCF SCYB8 IL8 | IL8 | 4q13–q21 |
| U09937 | 189_s_at | URKR UPAR CD87 | Source: Human urokinase-type plasminogen receptor, exon 7 | 19q13 |
| U27467 | 2002_s_at | BCL2L5 BFL1 GRS HBPA1 | Bcl-2 related; similar to mouse hemopoietic-specific early-response protein, Swiss-Prot Accession Number Q07440; similar to mouse transforming protein Bcl-2-β, Swiss-Prot Accession Number P10418; Method: conceptual translation | 15q24.3 |
| AL022315 | 37456_at | dJ117715.1 | supported by predicted exons match: ESTs: Em:AA316883 | 22q13.1 |
| M59465 | 595_at | TNFA1P2 A20 | tumor necrosis factor alpha inducible protein | 6 |
| U04636 | 1069_at | hCox-2 | Source: $H.$ $sapiens$ cyclooxygenase-2 (hCox-2) gene, complete cds | 1q25.2–q25.3 |

TABLE 5E

| Genbank | Common | Product | Keywords | Custom Field 2 |
|---|---|---|---|---|
| AL049963 | | | | D4S1572 |
| S68134 | CREM | cyclic AMP-responsive element modulator beta isoform | | D10S208 |
| M58603 | KBF1 | nuclear factor kappa-B DNA binding subunit | nuclear factor kappa-B DNA binding subunit | D4S1572 |
| M13755 | ISG15 | interferon-stimulated protein, 15 kDa | interferon; interferon-inducible protein | D8S264 |
| L31584 | EBI1 BLR2 CMKBR7 | chemokine (C—C motif) receptor 7 | G protein-coupled receptor | #N/A |
| AF022375 | VEGFA | vascular endothelial growth factor | | D6S282 |
| M58603 | KBF1 | nuclear factor kappa-B DNA binding subunit | nuclear factor kappa-B DNA binding subunit | D4S1572 |
| M58603 | KBF1 | nuclear factor of kappa light polypeptide gene enhancer in B-cells 1 (p105) | nuclear factor kappa-B DNA binding subunit | D4S1572 |
| U88964 | HEM45 | interferon stimulated gene 20 kD | | #N/A |
| L08177 | EBI2 | Epstein-Barr virus induced gene 2 (lymphocyte-specific G protein-coupled receptor) | | D13S1298 |
| D67031 | ADDL | adducin 3, isoform a | adducin-like protein; ADDL | D10S597 |
| AL021977 | HS5O6A DKFZP586A1024 | chromosome 22 open reading frame 5 | HTG; CpG island; MAFF | #N/A |
| V01512 | c-fos | v-fos FBJ murine osteosarcoma viral oncogene homolog | oncogene | #N/A |
| X59417 | IOTA PROS27 | prosomal P27K protein | PROS-27 gene; prosomal consensus; prosomal protein; RNA-binding protein | #N/A |
| X02910 | TNFA DIF TNFSF2 | tumor necrosis factor (cachectin) | signal peptide; tumor necrosis factor | #N/A |
| M15330 | IL1B | interleukin 1β | interleukin-1β | D2S160 |
| J04130 | MIP-1-BETA | small inducible cytokine A4 (homologous to mouse Mip-1β) | act2 gene; immune activation gene | D17S933 |
| M28130 | IL8 | interleukin 8 | interleukin 8 | #N/A |
| D90144 | MIPA SCYA3 | small inducible cytokine A3 (homologous to mouse Mip-1α) | LD78; LD78 alpha; cytokine; inducible gene family; secreted peptide | #N/A |
| S81914 | IEX-1 | immediate early response 3 | | D6S1660 |
| L11329 | PAC-1 PAC1 | protein tyrosine phosphatase | protein-tyrosine phosphatase; tyrosine phosphatase | D2S2264 |
| M57888 | CSPB CTLA1 CCPI CGL-1 CSP-B | granzyme B precursor | cytotoxic T-lymphocyte-associated serine esterase 1 | #N/A |
| M16441 | TNFSF1 TNFB LT | lymphotoxin alpha precursor | lymphotoxin; tumor necrosis factor | #N/A |
| X68277 | CL 100 | protein-tyrosine phosphatase | tyrosine phosphatase | #N/A |
| X78992 | ERF2 TIS11D | butyrate response factor 2 (EGF-response factor 2) | ERF-2 gene | D2S2259 |
| L12691 | DEF3 HNP-3 | defensin, alpha 3, neutrophil-specific | | #N/A |
| Z11697 | CD83 | CD83 antigen (activated B lymphocytes, immunoglobulin superfamily) | HB15 gene; immunoglobulin superfamily | D6S259 |
| M69199 | G0S2 | putative lymphocyte G0/G1 switch gene | G0S2 protein | #N/A |
| M17017 | MDNCF SCYB8 IL8 | interleukin 8 | beta-thromboglobulin | D4S3042 |
| U09937 | URKR UPAR CD87 | plasminogen activator, urokinase receptor | | #N/A |
| U27467 | BCL2L5 BFL1 GRS HBPA1 | BCL2-related protein A1 | | D15S1005 |
| AL022315 | dJ117715.1 | lectin, galactoside-binding, soluble, 2 (galectin 2) | HTG; CpG island; galectin; lectin LGALS2; MSE55 | #N/A |
| M59465 | TNFA1P2 A20 | tumor necrosis factor, alpha-induced protein 3 | | #N/A |
| U04636 | hCox-2 | cyclooxygenase-2 | | #N/A |

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for diagnosing responders to a glucocorticoid drug for treating asthma from non-responders to the drug, comprising:
   a) obtaining a sample of cells from a human patient;
   b) optionally inducing a pro-inflammatory-like state by treating the sample with specific mediators;
   c) obtaining a gene expression profile from the sample, wherein the expression profile comprises expression values for one or more genes listed in Tables 1, 2A, 2B, 4A, 4B and 5A–5E; and
   d) comparing the gene expression profile of the sample with a reference gene expression profile indicative of responsiveness to the drug obtained from one or more patients who are responsive to the drug and/or a reference gene expression profile indicative of non-responsiveness to the drug obtained from one or more patients who are non-responsive to the drug,
   wherein similarity in expression profiles between the sample and reference profiles indicates glucocorticoid sensitivity in the patient from whom the sample was obtained, thereby diagnosing the patient as a responder or non-responder to the drug.

2. The method of claim 1, wherein the expression profile comprises expression values for one or more genes listed in Tables 1, 2A and 2B.

3. The method of claim 1, wherein the expression profile comprises expression values for one or more genes listed in Tables 4A and 4B.

4. The method of claim 1, wherein the expression profile comprises expression values for one or more genes listed in Tables 5A–5E.

5. The method of claim 1, further comprising exposing the sample to the drug for treating asthma prior to obtaining the gene expression profile of the sample.

6. The method of claim 1, wherein the sample of cells is derived from peripheral blood mononuclear cells or neutrophils.

7. The method of claim 1, wherein the sample is obtained via biopsy from synovial membrane or airway smooth muscle.

8. The method of claim 1, wherein the gene expression profile of the sample is obtained using a hybridization assay to oligonucleotides contained in a microarray.

9. The method of claim 8 comprising the use of hybridization probes that hybridize to polynucleotides corresponding to informative genes and reagents for detecting hybridization.

10. The method of claim 1, wherein the reference expression profile is that of cells derived from patients who do not have asthma.

* * * * *